US011427845B2

(12) United States Patent
Jennewein

(10) Patent No.: US 11,427,845 B2
(45) Date of Patent: Aug. 30, 2022

(54) PRODUCTION OF OLIGOSACCHARIDES

(71) Applicant: Chr. Hansen HMO GmbH, Rheinbreitbach (DE)

(72) Inventor: Stefan Jennewein, Bad Honnef (DE)

(73) Assignee: Chr. Hansen HMO GmbH, Rheinbreitbach (DE)

( * ) Notice: Subject to any disclaimer, the term of this patent is extended or adjusted under 35 U.S.C. 154(b) by 0 days.

(21) Appl. No.: 15/067,037

(22) Filed: Mar. 10, 2016

(65) Prior Publication Data

US 2016/0186223 A1  Jun. 30, 2016

Related U.S. Application Data

(63) Continuation of application No. PCT/EP2014/064280, filed on Jul. 4, 2014.

(30) Foreign Application Priority Data

Sep. 10, 2013 (EP) .................................... 13183670

(51) Int. Cl.
| | |
|---|---|
| *C12N 1/20* | (2006.01) |
| *C12P 19/26* | (2006.01) |
| *C12P 19/14* | (2006.01) |
| *C07H 1/00* | (2006.01) |
| *C07H 1/06* | (2006.01) |
| *C12P 19/12* | (2006.01) |

(52) U.S. Cl.
CPC ............... *C12P 19/26* (2013.01); *C07H 1/00* (2013.01); *C07H 1/06* (2013.01); *C12P 19/12* (2013.01); *C12P 19/14* (2013.01); *C12Y 302/01* (2013.01)

(58) Field of Classification Search
CPC ......... C12P 19/18; C12N 1/20; C12N 9/1051; C12N 9/2405
See application file for complete search history.

(56) References Cited

U.S. PATENT DOCUMENTS

| | | | | |
|---|---|---|---|---|
| 2004/0121431 | A1* | 6/2004 | Kubota | C12N 9/1048 435/69.1 |
| 2008/0145899 | A1* | 6/2008 | Johnson | C12P 13/02 435/97 |
| 2010/0129843 | A1 | 5/2010 | Parsons et al. | |
| 2011/0300584 | A1* | 12/2011 | Hufner | C12N 9/1051 435/97 |
| 2012/0208181 | A1* | 8/2012 | Merighi | C12N 9/00 435/6.1 |
| 2013/0184180 | A1 | 7/2013 | Parsons et al. | |

FOREIGN PATENT DOCUMENTS

| | | |
|---|---|---|
| CN | 101657725 A | 2/2010 |
| CN | 101870992 A | 10/2010 |
| EP | 0682118 A2 | 11/1995 |
| EP | 2439264 A1 | 4/2012 |
| EP | 2479263 A1 | 7/2012 |
| EP | 2 728 009 A1 | 5/2014 |
| JP | 59095895 | 6/1984 |
| JP | 05276969 | 10/1993 |
| JP | 08140691 | 6/1996 |
| WO | WO 2009/113030 A1 | 9/2009 |
| WO | WO 2010/142305 A1 | 12/2010 |
| WO | WO 2011/016008 A1 | 2/2011 |
| WO | WO 2012/097950 A1 | 7/2012 |
| WO | WO 2012/112777 A2 | 8/2012 |
| WO | WO 2012/156897 A1 | 11/2012 |

OTHER PUBLICATIONS

B. Grossiord et al. "Genetics of galactose utilisation via the Leloir pathway in lactic acid bacteria" Le Lait, INRA Editions, 78 (1):77-84. (Year: 1998).*
Zhou et al., "Recombinant expression and characterization of *Thermoanaerobacter tengcongensis* thermostable α-glucosidase with regioselectivity for high-yield isomaltooligosaccharides synthesis," *Journal of Microbiology and Biotechnology*, 19(12): 1547-1556, published online Aug. 24, 2009.
Dumon et al. "Assessment of the Two Helicobacter pylori α-1-3-Fucosyltransferase Ortholog Genes for the Large-Scale Synthesis of LewisX Human Milk Oligosaccharides by Metabolically Engineered *Escherichia coli*" *Biotechnol. Prog.*, 20(2):412-419 (2004).
Dumon et al. "Production of Lewis x Tetrasaccharides by Metabolically Engineered *Escherichia coli*" *ChemBioChem*, 7:359-365 (2006).
The International Search Report from the parent PCT Application No. PCT/EP2014/064280 11 pages (dated Sep. 26, 2014).
Moreno et al., "A signal sequence is not sufficient to lead beta-galactosidase out of the cytoplasm," *Nature* 286:356-359, 1980.
Silhavy et al., "Conversion of beta-galactosidase to a membrane-bound state by gene fusion," *Proc Natl Acad Sci. USA* 73:3423-3427, 1976.
Baumgärtner et al., "Construction of *Escherichia coli* strains with chromosomally integrated expression cassettes for the synthesis of 2'-fucosyllactose," *Microbial Cell Factories* 12:40, 2013.
Lee et al., "trans-Sialidase catalyzed sialylation of β-galactosyldisaccaride with an introduction of β-galactosidase," *Enzyme and Microbial Technology* 28:161-167, 2001.
Lee et al., "Whole cell biosysnthesis of a functional oligosaccharide, 2'-fucosyllactose, using engineered *Escherichia coli,*" *Micobial Cell Factories* 11 (48):1-9, 2012.

(Continued)

*Primary Examiner* — Tekchand Saidha
(74) *Attorney, Agent, or Firm* — McNeill Baur PLLC

(57) ABSTRACT

The present invention relates to the use of one or more glycosidases in the process for the production and/or purification of a produced desired oligosaccharide. The process is preferably a microbial fermentation process using a host microorganism, which may also comprise nucleic acids expressing sugar catabolic pathway proteins suitable for the degradation of saccharides otherwise hindering the purification of the desired oligosaccharide.

12 Claims, 12 Drawing Sheets

Specification includes a Sequence Listing.

(56) References Cited

OTHER PUBLICATIONS

Marcobal et al., "Human milk oligosaccharide consumption by intestinal microbiota," *Clin Microbiol Infect* 18 (Suppl. 4): 12-15, 2012.
Nandakumar et al., "Proteomic analysis of extracellular proteins from *Escherichia coli* W3110," *J Proteome Res.* 5(5):1155-1161, 2006. (Abstract).
Schwab et al., "Lactic acid bacteria fermentation of human milk oligosaccharide components, human milk oligosaccharides and galactooligosaccharides," FEMS Microbiol Lett 315:141-148, 2011.
Wandersman, "Secretion, processing and activation of bacterial extracellular proteases," *Mol Microbiol.* 3(12): 1825-1831, 1989.
Zivkovic et al., "Human milk glycobiome and its impact on the infant gastrointestinal microbiota," *PNAS* 108, suppl. 1:4653-4658, 2011.
Extended European Search Report dated Oct. 29, 2019 for European Application No. 19184573.4 (12 pages).
Extended European Search Report dated Oct. 30, 2019 for European Application No. 19184576.7 (11 pages).
CN 101657725 A, US 2010/129843 A1 & US 2013/184180 A1.
CN 101870992 A, English Abstract attached to document.

* cited by examiner

Fig. 10

Sequence of the gal operon fragment (obtained from *E. coli* K strain JM109) and inserted into the employed *E. coli* BL21 (DE3) strain.

Sequence of used gal-operon fragment (SEQ ID No. 1)

```
TTACTCAGCAATAAACTGATATTCCGTCAGGCTGGAATACTCTTCGCCAGGACGCAGGAAGCAGTCCGGTTGCGGCCATTC
AGGGTGGTTCGGGCTGTCCGGTAGAAACTCGCTTTCCAGAGCCAGCCCTTGCCAGTCGGCGTAAGGTTCGGTTCCCCGCG
ACGGTGTGCCGCCGAGGAAGTTGCCGGAGTAGAATTGCAGAGCCGGAGCGGTGGTGTAGACCTTCAGCTGCAATTTTTCA
TCTGCTGACCAGACATGCGCCGCCACTTTCTTGCCATCGCCTTTGGCCTGTAACAAGAATGCGTGATCGTAACCTTTCACTT
TGCGCTGATCGTCGTCGGCAAGAAACTCACTGGCGATGATTTTGGCGCTGCGGAAATCAAAAGACGTTCCGGCGACAGAT
TTCAGGCCGTCGTGCGGAATGCCGCCTTCATCAACCGGCAGATATTCGTCCGCCAGAATCTGCAACTTGTGATTGCGCACG
TCAGACTGCTCGCCGTCAAGATTGAAATAGACGTGATTAGTCATATTCACCGGGCAAGGTTTATCAACTGTGGCGCGATAA
GTAATGGAGATACGGTTATCGTCGGTCAGACGATATTGCACCGTCGCGCCGAGATTACCCGGGAAGCCCTGATCACCATC
ATCTGAACTCAGGGCAAACAGCACCTGACGATCGTTCTGGTTCACAATCTGCCAGCGACGTTTGTCGAACCCTTCCGGCCC
GCCGTGCAGCTGGTTAACGCCCTGACTTGGCGAAAGCGTCACGGTTTCACCGTCAAAGGTATAACGGCTATTGGCGATAC
GGTTGGCATAACGACCAATAGAGGCCCCCAGAAACGCGGCCTGATCCTGATAGCATTCCGGGCTGGCACAGCCGAGCAG
CGCCTCGCGGACGCTGCCATCGGAAAGCGGAATACGGGCGGAAAGTAAAGTCGCACCCCAGTCCATCAGCGTGACTACC
ATCCCTGCGTTGTTACGCAAAGTTAACAGTCGGTACGGCTGACCATCGGGTGCCAGTGCGGGAGTTTCGTTCAGCACTGTC
CTGCTCCTTGTGATGGTTTACAAACGTAAAAAGTCTCTTTAATACCTGTTTTTGCTTCATATTGTTCAGCGACAGCTTGCTGT
ACGGCAGGCACCAGCTCTTCCGGGATCAGCGCGACGATACAGCCGCCAAATCCGCCGCCGGTCATGCGTACGCCACCTT
TGTCGCCAATCACAGCTTTGACGATTTCTACCAGAGTGTCAATTTGCGGCACGGTGATTTCGAAATCATCGCGCATAGAGG
CATGAGACTCCGCCATCAACTCGCCCATACGTTTCAGGTCGCCTTGCTCCAGCGCGCTGGCAGCTTCAACGGTGCGGGCG
TTTTCAGTCAGTATATGACGCACGCGTTTTGCCACGATCGGGTCCAGTTCATGCGCAACAGCGTTGAACTCTTCAATGGTGA
CATCACGCAGGGCTGGCTGCTGGAAGAAACGCGCACCGGTTTCGCACTGTTCACGACGGGTGTTGTATTCGCTGCCAACC
AGGGTACGTTTGAAGTTACTGTTGATGATGACGACAGCCACACCTTTGGGCATGGAAACTGCTTTGGTCCCCAGTGAGCGG
CAATCGATCAGCAAGGCATGATCTTTCTTGCCGAGCGCGGAAATTAGCTGATCCATGATCCCGCAGTTACAGCCTACAAAC
TGGTTTTCTGCTTCCTGACCGTTAAGCGCGATTTGTGCGCCGTCCAGCGGCAGATGATAAAGCTGCTGCAATACGGTTCCG
ACCGCGACTTCCAGTGAAGCGGAAGAACTTAACCCGGCACCCTGCGGCACATTGCCGCTGATCACCATGTCCACGCCGCC
GAAGCTGTTGTTACGCAGTTGCAGATGTTTCACCACGCCACGAACGTAGTTAGCCCATTGATAGTTTTCATGTGCGACAATG
GGCGCATCGAGGGAAAACTCGTCGAGCTGATTTTCATAATCGGCTGCCATCACGCGAACTTTACGGTCATCGCGTGGTGCA
CAACTGATCACGGTTTGATAATCAATCGCGCAGGGCAGAACGAAACCGTCGTTGTAGTCGGTGTGTTCACCAATCAAATTC
ACGCGGCCAGGCGCCTGAATGGTGTGAGTGGCAGGGTAGCCAAATGCGTTGGCAAACAGAGATTGTGTTTTTTCTTTCAGA
CTCATTTCTTACACTCCGGATTCGCGAAAATGGATATCGCTGACTGCGCGCAAACGCTCTGCTGCCTGTTCTGCGGTCAGG
TCTCGCTGGGTCTCTGCCAGCATTTCATAACCAACCATAAATTTACGTACGGTGGCGGAGCGCAGCAGAGGCGGATAAAAG
TGCGCGTGCAGCTGCCAGTGTTGATTCTCTTCGCCATTAAATGGCGCGCCGTGCCAGCCCATAGAGTAGGGGAAGGAGCA
CTGGAAGAGGTTGTCATAACGACTGGTCAGCTTTTTCAACGCCAGCGCCAGATCGCTGCGCTGGGCGTCGGTCAAATCGG
TGATCCGTAAAACGTGGGCTTTGGGCAGCAGTAGCGTTTCGAACGGCCAGGCAGCCCAGTAAGGCACGACGGCTAACCAG
TGTTCGGTTTCGACAACGGTACGGCTACCGTCTGCCAGCTCGCGCTGAACATAATCCACCAGCATTGGTGATTTCTGTTCG
GCAAAATATTCTTTTTGCAGGCGGTCTTCGCGCTCAGCTTCGTTAGGCAGGAAGCTATTTGCCCAAATCTGACCGTGCGGA
TGCGGGTTAGAGCAGCCCATCGCCGCGCCTTTGTTTTCAAAAACCTGCACCCATGGGTACGTTTCCCCAGTTCTGCGGTT
TGCTCCTGCCAGGTTTTGACGATTTCCGTCAATGCTGCAACGCTGAGCTCTGGCAGCGTTTTACTGTGATCCGGTGAAAAG
CAGATCACCCGGCTGGTGCCGCGCGCGCTCTGGCAACGCATCAGCGGATCGTGACTTTCTGGCGCATCTGGCGTGTCAG
ACATCAAAGCCGCAAAGTCATTAGTGAAAACGTAAGTCCCGGTGTAATCGGGGTTTTTATCGCCTGTCACCCGCACATTACC
```

Fig. 10 (continued)

```
TGCGCAGAGGAAGCAATCTGGATCGTGCGCAGGTAACACCTGTTTGGCTGGCGTTTCCTGCGCCCCCTGCCAGGGGCGC
TTAGCGCGGTGCGGTGAAACCAGAATCCATTGCCCGGTGAGCGGGTTGTAGCGGCGATGTGGATGATCAACGGGATTAAA
TTGCGTCATGGTCGTTCCTTAATCGGGATATCCCTGTGGATGGCGTGACTGCCAGTGCCAGGTGTCCTGCGCCATTTCATC
GAGTGTGCGCGTTACGCGCCAGTTCAGTTCACGGTCGGCTTTGCTGGCGTCCGCCCAGTAGGCCGGAAGGTCGCCCTCG
CGACGCGGTGCAAAATGATAATTAACCGGTTTGCCGCAGGCTTTGCTGAAGGCATTAACCACGTCCAGCACGCTGTTGCCT
ACGCCAGCGCCGAGGTTGTAGATGTGTACGCCTGGCTTGTTCGCCAGTTTTTCCATCGCCACGACGTGACCGTCCGCCAG
ATCCATTACGTGGATGTAATCGCGTACGCCAGTACCATCTTCGGTCGGATAATCGTTACCAAAAATCGCCAGCGAGTCGCG
ACGGCCTACAGCAACCTGGGCGATGTATGGCATCAGGTTATTCGGAATGCCTTGCGGATCTTCGCCCATATCGCCCGACG
GATGCGCGCCAACCGGGTTGAAGTAGCGCAGCAGGGCAATGCTCCAGTCCGGCTGGGCTTTTTGCAGATCGGTGAGGAT
CTGTTCCACCATCAGCTTGCTTTTGCCGTAAGGGCTTTGCGGTGTGCCGGTCGGGAAGCTTTCAACGTATGGAATTTTGGG
CTGATCGCCATAAACGGTGGCGGAGGAGCTAAAAATAAAGTTTTTGACGTTAGCGGCGCGCATGGCGCTAATCAGGCGCA
GAGTGCCGTTGACATTGTTGTCGTAATATTCCAGCGGTTTTTGTACCGATTCGCCCACGGCTTTCAGCCCGGCGAAGTGGA
TCACGGTGTCGATAGCGTGATCGTGCAGGATCTCGGTCATCAACGCTTCGTTACGAATATCGCCTTCAACAAACGTTGGAT
GTTTGCCGCCTAAACGCTCGATAACAGGCAGTACGCTGCGCTTACTGTTACAGAGGTTATCAAGAATGATGACATCATGAC
CGTTTTGCAGTAATTGCACACAGGTATGACTTCCAATGTAACCGCTACCACCGGTAACCAGAACTCTCATAATTCGCTCCAT
TAGGCTTATGGTATGAAATAACCATAGCATAACAAAGATGCGAAAAGTGTGACATGGAATAAATTAGTGGAATCGTTTACAC
AAGAATTTAGCCGTTTTTTATGCGCGATTAAGTGATTATAAAACAGAGGGTTTATGAATGATTGCGCTTTTTATCTGAAAAAA
GACGCGGTTTCATGCCTGCATGCGTCGAACCGTTGGCCGGAGAGGGTGCTAAGGCCGCCTCCGGCAAGGTCAGCACTAC
CGACGTTAACGGAAATTACGCTCTATATGGAAAGTCTGACTGCTGAAGAGCGCGAGATTATCAA
```

Fig. 11

Table 1: list of oligosaccharides that can be produced according to the invention

| No. | Name | Abbreviation | Oligosaccharide |
|---|---|---|---|
| 1 | 2'-Fucosyllactose | 2'-FL | Fuc($\alpha$1-2)Gal($\beta$1-4)Gluc |
| 2 | 3-Fucosyllactose | 3-FL | Gal($\beta$1-4)Gluc<br>\|<br>Fuc($\alpha$1-3) |
| 3 | 2',3-Difucosyllactose | DF-L | Fuc($\alpha$1-2)Gal($\beta$1-4)Gluc<br>\|<br>Fuc($\alpha$1-3) |
| 5 | Lacto-*N*-triose II | LNT II | GlcNAc($\beta$1-3)Gal($\beta$1-4)Gluc |
| 6 | Lacto-*N*-tetraose | LNT | Gal($\beta$1-3)GlcNAc($\beta$1-3)Gal($\beta$1-4)Gluc |
| 7 | Lacto-*N-neo*tetraose | LNnT | Gal($\beta$1-4)GlcNAc($\beta$1-3)Gal($\beta$1-4)Gluc |
| 8 | Lacto-*N*-fucopentaose I | LNFP I | Fuc($\alpha$1-2)Gal($\beta$1-3)GlcNAc($\beta$1-3)Gal($\beta$1-4)Gluc |
| 9 | Lacto-*N-neo*fucopentaose I | LNnFP I | Fuc($\alpha$1-2)Gal($\beta$1-4)GlcNAc($\beta$1-3)Gal($\beta$1-4)Gluc |
| 10 | Lacto-*N*-fucopentaose II | LNFP II | Gal($\beta$1-3)GlcNAc($\beta$1-3)Gal($\beta$1-4)Gluc<br>\|<br>Fuc($\alpha$1-4) |
| 11 | Lacto-*N*-fucopentaose III | LNFP III | Gal($\beta$1-4)GlcNAc($\beta$1-3)Gal($\beta$1-4)Gluc<br>\|<br>Fuc($\alpha$1-3) |
| 12 | Lacto-*N*-fucopentaose V | LNFP V | Gal($\beta$1-3)GlcNAc($\beta$1-3)Gal($\beta$1-4)Gluc<br>\|<br>Fuc($\alpha$1-3) |
| 13 | Lacto-*N-neo*fucopentaose V | LNnFP V | Gal($\beta$1-4)GlcNAc($\beta$1-3)Gal($\beta$1-4)Gluc<br>\|<br>Fuc($\alpha$1-3) |
| 14 | Lacto-*N*-difucohexaose I | LNDH I | Gal($\beta$1-3)GlcNAc($\beta$1-3)Gal($\beta$1-4)Gluc<br>\| \|<br>Fuc($\alpha$1-2) Fuc($\alpha$1-4) |
| 15 | Lacto-*N*-difucohexaose II | LND | Gal($\beta$1-3)GlcNAc($\beta$1-3)Gal($\beta$1-4)Gluc<br>\| \|<br>Fuc($\alpha$1-4) Fuc($\alpha$1-3) |
| 16 | 6'-Galactosyllactose | 6'-GL | Gal($\beta$1-6)Gal($\beta$1-4)Gluc |
| 17 | 3'-Galactosyllactose | 3'-GL | Gal($\beta$1-3)Gal($\beta$1-4)Gluc |
| 18 | Lacto-*N*-hexaose | LNH | Gal($\beta$1-4)GlcNAc($\beta$1-6)Gal($\beta$1-4)Gluc<br>\|<br>Gal($\beta$1-3)GlcNAc($\beta$1-3) |
| 19 | Lacto-*N-neo*hexaose | LNnH | Gal($\beta$1-4)GlcNAc($\beta$1-6)Gal($\beta$1-4)Gluc<br>\|<br>Gal($\beta$1-4)GlcNAc($\beta$1-3) |

Fig. 11 (continued)

| # | Name | Abbrev. | Structure |
|---|---|---|---|
| 20 | *para*-Lacto-*N*-hexaose | paraLNT | Gal(β1-3)GlcNAc(β1-3)Gal(β1-4)GlcNAc(β1-3)Gal(β1-4)Gluc |
| 21 | *para*-Lacto-*N-neo*hexaose | paraLNnH | Gal(β1-4)GlcNAc(β1-3)Gal(β1-4)GlcNAc(β1-3)Gal(β1-4)Gluc |
| 22 | Difucosyl-lacto-*N-neo*hexaose | DF-LNnH | Fuc(α1-3)<br>\|<br>Gal(β1-4)GlcNAc(β1-6)Gal(β1-4)Glc<br>\|<br>Gal(β1-4)GlcNAc(β1-3)<br>\|<br>Fuc(α1-3) |
| 23 | 3'-Sialyllactose | 3'-SL | Neu5Ac(α2-3)Gal(β1-4)Gluc |
| 24 | 6'-Sialyllactose | 6'-SL | Neu5Ac(α2-6)Gal(β1-4)Gluc |
| 25 | Lacto-*N*-sialylpentaose a | LST-a | Neu5Ac(α2-3)Gal(β1-3)GlcNAc(β1-3)Gal(β1-4)Gluc |
| 26 | Lacto-*N*-sialylpentaose b | LST-b | Gal(β1-3)GlcNAc(β1-3)Gal(β1-4)Gluc<br>\|<br>Neu5Ac(α2-6) |
| 27 | Lacto-*N*-sialylpentaose c | LST-c | Neu5Ac(α2-6)Gal(β1-4)GlcNAc(β1-3)Gal(β1-4)Gluc |
| 28 | Fucosyl-lacto-*N*-sialylpentaose a | F-LST-a | Neu5Ac(α2-3)Gal(β1-3)GlcNAc(β1-3)Gal(β1-4)Gluc<br>\|<br>Fuc(α1-4) |
| 29 | Fucosyl-lacto-*N*-sialylpentaose b | F-LST-b | Fuc(α1-2)Gal(β1-3)GlcNAc(β1-3)Gal(β1-4)Gluc<br>\|<br>Neu5Ac(α2-6) |
| 30 | Fucosyl-lacto-*N*-sialylpentaose c | F-LST-c | Neu5Ac(α2-3)Gal(β1-3)GlcNAc(β1-3)Gal(β1-4)Gluc<br>\|<br>Fuc(α1-3) |
| 31 | Disialyl-lacto-*N*-tetraose | DS-LNT | Neu5Ac(α2-3)Gal(β1-4)GlcNAc(β1-3)Gal(β1-4)Gluc<br>\|<br>Neu5Ac(α2-6) |
| 32 | Disialyl-lacto-*N*-fucopentaose | DS-LNFP V | Neu5Ac(α2-3)Gal(β1-4)GlcNAc(β1-3)Gal(β1-4)Gluc<br>\| \|<br>Neu5Ac(α2-6)   Fuc(α1-3) |
| 33 | 3-Fucosyl-3'-sialyllactose | 3F-3'-SL | Neu5Ac(α2-3)Gal(β1-4)Gluc<br>\|<br>Fuc(α1-3) |
| 34 | 3-Fucosyl-6'-sialyllactose | 3F-6'-SL | Neu5Ac(α2-6)Gal(β1-4)Gluc<br>\|<br>Fuc(α1-3) |
| 35 | Lacto-*N-neo*difucohexaose I | LNnDFH I | Gal(β1-4)GalNAc(β1-3)Gal(β1-4)Glc<br>\| \|<br>Fuc(α1-3)   Fuc(α1-3) |

SEQUENCE LISTING

<160> NUMBER OF SEQ ID NOS: 3

<210> SEQ ID NO 1
<211> LENGTH: 4579
<212> TYPE: DNA
<213> ORGANISM: Escherichia coli

<400> SEQUENCE: 1

| | | | | | |
|---|---|---|---|---|---|
| ttactcagca | ataaactgat | attccgtcag | gctggaatac | tcttcgccag | gacgcaggaa | 60 |
| gcagtccggt | tgcggccatt | cagggtggtt | cgggctgtcc | ggtagaaact | cgctttccag | 120 |
| agccagccct | tgccagtcgg | cgtaaggttc | ggttccccgc | gacggtgtgc | cgccgaggaa | 180 |
| gttgccggag | tagaattgca | gagccggagc | ggtggtgtag | accttcagct | gcaattttc | 240 |
| atctgctgac | cagacatgcg | ccgccacttt | cttgccatcg | cctttggcct | gtaacaagaa | 300 |
| tgcgtgatcg | taacctttca | ctttgcgctg | atcgtcgtcg | gcaagaaact | cactggcgat | 360 |
| gattttggcg | ctgcggaaat | caaaagacgt | tccggcgaca | gatttcaggc | cgtcgtgcgg | 420 |
| aatgccgcct | tcatcaaccg | gcagatattc | gtccgccaga | atctgcaact | tgtgattgcg | 480 |
| cacgtcagac | tgctcgccgt | caagattgaa | atagacgtga | ttagtcatat | tcaccgggca | 540 |
| aggtttatca | actgtggcgc | gataagtaat | ggagatacgg | ttatcgtcgg | tcagacgata | 600 |
| ttgcaccgtc | gcgccgagat | tacccgggaa | gccctgatca | ccatcatctg | aactcagggc | 660 |
| aaacagcacc | tgacgatcgt | tctggttcac | aatctgccag | cgacgtttgt | cgaacccttc | 720 |
| cggcccgccg | tgcagctggt | taacgccctg | acttggcgaa | agcgtcacgg | tttcaccgtc | 780 |
| aaaggtataa | cggctattgg | cgatacggtt | ggcataacga | ccaatagagg | ccccagaaa | 840 |
| cgcggcctga | tcctgatagc | attccgggct | ggcacagccg | agcagcgcct | cgcggacgct | 900 |
| gccatcggaa | agcggaatac | gggcggaaag | taaagtcgca | ccccagtcca | tcagcgtgac | 960 |
| taccatccct | gcgttgttac | gcaaagttaa | cagtcggtac | ggctgaccat | cgggtgccag | 1020 |
| tgcgggagtt | tcgttcagca | ctgtcctgct | ccttgtgatg | gtttacaaac | gtaaaaagtc | 1080 |
| tctttaatac | ctgttttttgc | ttcatattgt | tcagcgacag | cttgctgtac | ggcaggcacc | 1140 |
| agctcttccg | ggatcagcgc | gacgatacag | ccgccaaatc | cgccgccggt | catgcgtacg | 1200 |
| ccacctttgt | cgccaatcac | agctttgacg | atttctacca | gagtgtcaat | ttgcggcacg | 1260 |
| gtgatttcga | atcatcgcg | catagaggca | tgagactccg | ccatcaactc | gcccatacgt | 1320 |
| ttcaggtcgc | cttgctccag | cgcgctggca | gcttcaacgg | tgcgggcgtt | ttcagtcagt | 1380 |
| atatgacgca | cgcgttttgc | cacgatcggg | tccagttcat | gcgcaacagc | gttgaactct | 1440 |
| tcaatggtga | catcacgcag | ggctggctgc | tggaagaaac | gcgcaccggt | ttcgcactgt | 1500 |
| tcacgacggg | tgttgtattc | gctgccaacc | agggtacgtt | tgaagttact | gttgatgatg | 1560 |
| acgacagcca | cacctttggg | catggaaact | gctttggtcc | ccagtgagcg | gcaatcgatc | 1620 |
| agcaaggcat | gatcttcttc | gccgagcgcg | gaaattagct | gatccatgat | cccgcagtta | 1680 |
| cagcctacaa | actggttttc | tgcttcctga | ccgttaagcg | cgatttgtgc | gccgtccagc | 1740 |
| ggcagatgat | aaagctgctg | caatacggtt | ccgaccgcga | cttccagtga | agcggaagaa | 1800 |
| cttaaccccgg | cacctgcgg | cacattgccg | ctgatcacca | tgtccacgcc | gccgaagctg | 1860 |
| ttgttacgca | gttgcagatg | tttcaccacg | ccacgaacgt | agttagccca | ttgatagttt | 1920 |
| tcatgtgcga | caatgggcgc | atcgagggaa | aactcgtcga | gctgattttc | ataatcggct | 1980 |
| gccatcacgc | gaactttacg | gtcatcgcgt | ggtgcacaac | tgatcacggt | ttgataatca | 2040 |
| atcgcgcagg | gcagaacgaa | accgtcgttg | tagtcggtgt | gttcaccaat | caaattcacg | 2100 |

```
cggccaggcg cctgaatggt gtgagtggca gggtagccaa atgcgttggc aaacagagat    2160 tgtgttttt  ctttcagact catttcttac actccggatt cgcgaaaatg gatatcgctg    2220
actgcgcgca aacgctctgc tgcctgttct gcggtcaggt ctcgctgggt ctctgccagc    2280
atttcataac caaccataaa tttacgtacg gtggcggagc gcagcagagg cggataaaag    2340
tgcgcgtgca gctgccagtg ttgattctct tcgccattaa atggcgcgcc gtgccagccc    2400
atagagtagg ggaaggagca ctggaagagg ttgtcataac gactggtcag cttttcaac    2460 gccagcgcca gatcgctgcg ctgggcgtcg gtcaaatcgg tgatccgtaa aacgtgggct    2520
ttgggcagca gtagcgtttc gaacggccag gcagcccagt aaggcacgac ggctaaccag    2580
tgttcggttt cgacaacggt acggctaccg tctgccagct cgcgctgaac ataatccacc    2640
agcattggtg atttctgttc ggcaaaatat tcttttttgca ggcggtcttc gcgctcagct    2700
tcgttaggca ggaagctatt tgcccaaatc tgaccgtgcg gatgcgggtt agagcagccc    2760
atcgccgcgc ctttgttttc aaaaacctgc acccatgggg acgttttccc cagttctgcg    2820
gtttgctcct gccaggtttt gacgatttcc gtcaatgctg caacgctgag ctctggcagc    2880
gttttactgt gatccggtga aaagcagatc acccggctgg tgccgcgcgc gctctggcaa    2940
cgcatcagcg gatcgtgact ttctggcgca tctggcgtgt cagacatcaa agccgcaaag    3000
tcattagtga aaacgtaagt cccggtgtaa tcggggtttt tatcgcctgt cacccgcaca    3060
ttacctgcgc agaggaagca atctggatcg tgcgcaggta acacctgttt ggctggcgtt    3120
tcctgcgccc cctgccaggg gcgcttagcg cggtgcggtg aaaccagaat ccattgcccg    3180
gtgagcgggt tgtagcggcg atgtggatga tcaacgggat taaattgcgt catggtcgtt    3240
ccttaatcgg gatatccctg tggatggcgt gactgccagt gccaggtgtc ctgcgccatt    3300
tcatcgagtg tgcgcgttac gcgccagttc agttcacggt cggctttgct ggcgtccgcc    3360
cagtaggccg gaaggtcgcc ctcgcgacgc ggtgcaaaat gataattaac cggtttgccg    3420
caggctttgc tgaaggcatt aaccacgtcc agcacgctgt tgcctacgcc agcgccgagg    3480
ttgtagatgt gtacgcctgg cttgttcgcc agttttttcca tcgccacgac gtgaccgtcc    3540
gccagatcca ttacgtggat gtaatcgcgt acgccagtac catcttcggt cggataatcg    3600
ttaccaaaaa tcgccagcga gtcgcgacgg cctacagcaa cctgggcgat gtatggcatc    3660
aggttattcg gaatgccttg cggatcttcg cccatatcgc ccgacggatg cgcgccaacc    3720
gggttgaagt agcgcagcag ggcaatgctc cagtccggct gggcttttg cagatcggtg    3780 aggatctgtt ccaccatcag cttgcttttg ccgtaagggc tttgcggtgt gccggtcggg    3840
aagctttcaa cgtatggaat tttgggctga tcgccataaa cggtggcgga ggagctaaaa    3900
ataaagtttt tgacgttagc ggcgcgcatg gcgctaatca ggcgcagagt gccgttgaca    3960
ttgttgtcgt aatattccag cggttttttgt accgattcgc ccacggcttt cagcccggcg    4020
aagtggatca cggtgtcgat agcgtgatcg tgcaggatct cggtcatcaa cgcttcgtta    4080
cgaatatcgc cttcaacaaa cgttggatgt ttgccgccta aacgtcgat aacaggcagt    4140 acgctgcgct tactgttaca gaggttatca agaatgatga catcatgacc gttttgcagt    4200
aattgcacac aggtatgact tccaatgtaa ccgctaccac cggtaaccag aactctcata    4260
attcgctcca ttaggcttat ggtatgaaat aaccatagca taacaaagat gcgaaaagtg    4320
tgacatggaa taaattagtg gaatcgttta cacaagaatt tagccgtttt ttatgcgcga    4380
ttaagtgatt ataaaacaga gggtttatga atgattgcgc ttttatctg aaaaaagacg    4440
```

-continued

```
cggtttcatg cctgcatgcg tcgaaccgtt ggccggagag ggtgctaagg ccgcctccgg    4500
caaggtcagc actaccgacg ttaacggaaa ttacgctcta tatggaaagt ctgactgctg    4560
aagagcgcga gattatcaa                                                 4579

<210> SEQ ID NO 2
<211> LENGTH: 35
<212> TYPE: DNA
<213> ORGANISM: Artificial sequence
<220> FEATURE:
<223> OTHER INFORMATION: forward primer

<400> SEQUENCE: 2
ttactcagca ataaactgat attccgtcag gctgg                                 35

<210> SEQ ID NO 3
<211> LENGTH: 86
<212> TYPE: DNA
<213> ORGANISM: Artificial sequence
<220> FEATURE:
<223> OTHER INFORMATION: reverse primer

<400> SEQUENCE: 3
ttgataatct cgcgctcttc agcagtcaga ctttccatat agagcgtaat ttccgttaac    60
gtcggtagtg ctgaccttgc cggagg                                          86
```

PRODUCTION OF OLIGOSACCHARIDES

CROSS REFERENCE TO RELATED APPLICATIONS

This application is a continuation of international patent application PCT/EP2014/064280, filed on Jul. 4, 2014, designating the U.S., which international patent application has been published in English language and claims priority from European patent application 13 183 670.2, filed on Sep. 10, 2013. The entire contents of these priority applications are incorporated herein by reference.

BACKGROUND OF THE INVENTION

The present invention generally relates to the processes for the production of oligosaccharides or polysaccharides, such as, e.g., the production of oligosaccharides or polysaccharides via microbial fermentation, and in particular to the use of hydrolases in such processes.

The commercial production of oligosaccharides has—together with the development of novel manufacturing biotechnologies—become of increasing interest over the past years. Today, oligosaccharides are used, e.g., as functional food ingredients, nutritional additives, or as nutraceuticals. Traditionally, oligosaccharides are defined as polymers of 2 or more (usually up to 10) monosaccharides, however, also polymers up to 20 to 25 are often assimilated with them. In particular prebiotic oligosaccharides are of high interest, since they represent noncariogenic and nondigestible compounds stimulating the growth and development of human gastrointestinal microflora.

Currently, oligosaccharides are either synthesized by chemical glycosylation and de novo using glycosyltransferases, or they can derive from chemical, physical or biological degradation of polysaccharides.

Today, fructooligosaccharides and galactooligosaccharides synthesized or isolated from plant polysaccharides represent the most abundantly produced oligosaccharides. However, due to superior health benefits the interest in Human Milk Oligosaccharides (HMO) as nutraceuticals has strongly increased over the past years. It is well established that HMOs contribute to the human body's defense mechanism against human pathogens, the establishment of a particular intestinal flora (microbiome), and postnatal stimulation of the immune system. Although HMOs are consumed by infants, it is accepted that the beneficial effects of these oligosaccharides observed during the postnatal period can be also found later in life.

It has been long known that human mother's milk, besides lactose, comprises a complex mixture of oligosaccharides called Human Milk Oligosaccharides (HMO) represents a complex mixture of oligosaccharides being unique with respect to composition and quantity. Today, more than 80 HMO compounds have been structurally characterized, and, with few exceptions, they are characterized by a lactose moiety at the reducing end and often containing a fucose and/or sialic acid at the non-reducing end. Generally the monosaccharides from which HMOs are derived are D-glucose, D-galactose, N-acetylglucosamine, L-fucose and sialic acid.

The most prominent oligosaccharides are 2'-fucosyllactose and 3'-fucosyllactose which together can contribute up to ⅓ of the total HMO fraction. Further prominent HMOs present in human milk are lacto-N-tetraose, lacto-N-neotetraose and the lacto-N-fucopentaoses. Besides these neutral oligosaccharides, also acidic HMOs can be found in human milk, like for e.g. 3'-sialyllactose, 6'-sialyllactose and 3-fucosyl-3'-sialyllactose, disialyl-lacto-N-tetraose etc. These structures are closely related to epitopes of epithelial cell surface glycoconjugates, the Lewis histoblood group antigens such as Lewis x (LeX), and the structural homology of HMO to epithelial epitopes accounts for protective properties against bacterial pathogens.

Besides the mentioned local effects in the intestinal tract, HMOs have also been shown to elicit systemic effects in infants by entering the systemic circulation. Also, the impact of HMOs on protein-carbohydrate interactions, e.g., selectin-leukocyte binding, can modulate immune responses and reduce inflammatory responses.

Due to the well-studied beneficial properties of prebiotic oligosaccharides, in particular of HMOs, connected with their limited availability, an effective commercial, i.e. large scale production is highly desirable.

The main drawback today, however, is in most cases the lack of effective oligosaccharide production. As mentioned above, oligosaccharides can be generated from oligomer engineering with either synthesis, using enzymatic or chemical engineering, or polysaccharide depolymerization, using physical, chemical or enzymatic methods.

Chemical synthesis of oligosaccharides has proved to be challenging due to the presence of several hydroxyl groups of similar chemical reactivity. Thus, in chemical synthesis of oligosaccharides saccharide building blocks have firstly to be selectively protected in order to control the reactivity of the chemically similar groups, then coupled, and finally de-protected to obtain the desired oligosaccharide. Even if the small-scale synthesis of a desired oligosaccharide is possible, the developed synthetic routes are in general time-consuming, technically challenging and often prohibitively expensive. Enzymatic synthesis or the combination of chemical and enzymatic synthesis offer significant advantages over pure chemical synthetic routes. Several human milk oligosaccharides such as 2'-fucosyllactose, lacto-N-tetraose lacto-N-neotetraose or 3'-sialyllactose were already obtained by enzymatic synthesis. Besides the enzymatic synthesis also fermentative approaches to oligosaccharides proved successful, and several oligosaccharides—including HMOs—have been made available in considerable yields by fermentative means.

Further, with a chemical or biochemical synthesis of oligosaccharidic structures, which, as mentioned before, is much more difficult than, e.g. the synthesis of other biopolymers such as peptides and nucleic acids, often oligosaccharides mixtures are produced containing non-desired oligosaccharides which need to be separated or removed from the desired oligosaccharide. Same applies for oligosaccharides generated via microbial fermentation, since during those processes a high amount of by-products, intermediate products or even starting substrates is to be found in the reaction mixture/cell medium containing the to be fermented microorganisms.

Against this background, there exists a great need for effective methods and processes for the production of a desired oligosaccharide, in particular of HMOs, the efficient production bearing high medical relevance and as well commercial impact.

SUMMARY OF THE INVENTION

This and other objects has been solved by the present invention by the use of one or more glycosidases in the purification of a produced desired oligosaccharide from a mixture containing the produced desired oligosaccharide and, where applicable, non-desired oligosaccharides or metabolic saccharide products generated during production of said desired oligosaccharide, and/or unused saccharide substrates used in the production of said oligosaccharide, for degradation of the non-desired oligosaccharides or metabolic products or unused substrates.

The object is further solved by a process for producing an oligosaccharide using a host microorganism, wherein said oligosaccharide is not naturally occurring in said host cell, the process comprising the steps of a) cultivating a host microorganism suitable for the production of a desired oligosaccharide under conditions and in a medium permissive for the production of said oligosaccharide, whereby the oligosaccharide and, where applicable, biosynthetic intermediates and/or side products are produced; b) using a glycosidase in the medium the host microorganism is cultivated in, in order to degrade biosynthetic saccharide intermediates and/or saccharide side products and/or unused saccharide substrates, and c) recovering the desired oligosaccharide.

According to the invention, a glycosidase is applied in the process for the production of a oligosaccharide, wherein the glycosidase is used for degrading hindering and/or undesired side-products, unused starting substrates and intermediate products generated during the production of the desired oligosaccharide; thus, according to the invention, the glycosidase is employed for purification of the desired oligosaccharide from a mixture containing the desired oligosaccharide and other unwanted carbohydrate moieties.

According to the invention, the glycosidase can be used in fermentation processes producing a desired oligosaccharide as well as for the purification or resolution of oligosaccharide mixtures obtained by in vitro oligosaccharide synthesis reactions or by chemical synthesis or combinations thereof.

By means of the glycosidase it can be achieved that, e.g. other (oligo-) saccharides—besides the desired oligosaccharide-, which other (oligo-)saccharides are produced in the microorganism during the synthesis of the desired oligosaccharide, and which other oligosaccharides interfere with the purification step of the desired oligosaccharide, can be metabolised.

BRIEF DESCRIPTION OF THE DRAWINGS

Several embodiments of the invention are illustrated in the figures and explained in more detail in the following description. In the figures:

FIG. 1A. shows the superimposed HPLC chromatograms of 10 mM lactose and 10 mM lacto-N-tetraose (authentic standards). FIG. 1B is a HPLC chromatogram of beta-galactosidase reaction containing 10 mM lactose and 10 mM lacto-N-tetraose immediately taken after enzyme addition. FIG. 1C is a HPLC chromatogram of beta-galactosidase reaction containing 10 mM lactose and 10 mM lacto-N-tetraose taken 3 hours post enzyme addition;

FIG. 10 shows the sequence of the gal operon used in the generation of the recombinant E. coli strains; and FIG. 11 shows a list of oligosaccharides that can be produced according to the invention.

SEQUENCE LISTING

Figures 1A, 1B, 1C:
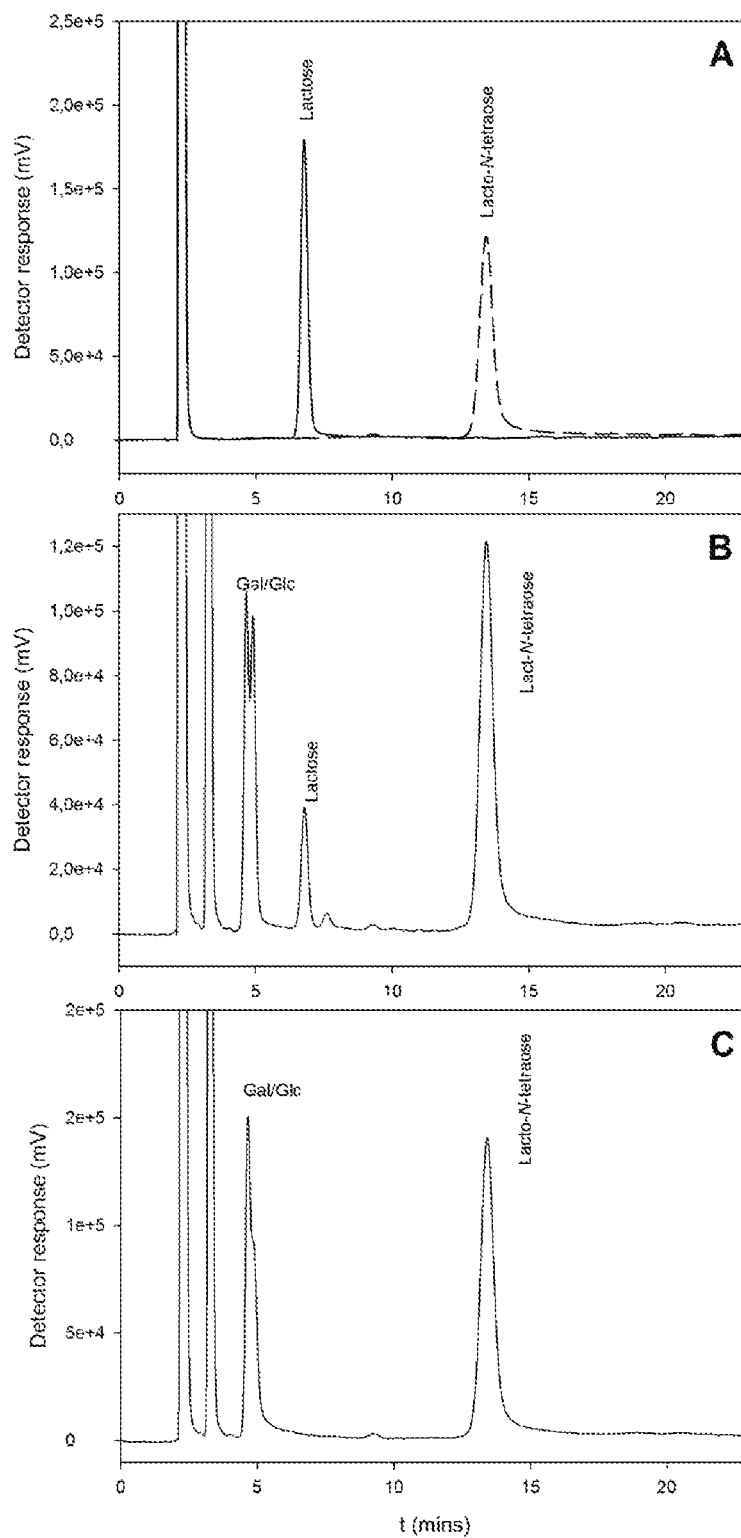
FIGS. 1A, 1B and 1C show the resolution of lacto-N-tetraose and lactose using a beta-galactosidase.

The Sequence Listing is submitted as an ASCII text file [7291-96601-01_Sequence_Listing.txt, Mar. 10, 2016, 7 KB], which is incorporated by reference herein.

DETAILED DESCRIPTION

The use of a glycosidase in a process for the production of a desired oligosaccharide has not been described so far. To the contrary: In the processes currently applied, i.e. for the fermentation of HMO, usually lactose is added as a substrate for the synthesis. To prevent the degradation of the added lactose beta-galactosidase, as well as other glycosidase reactions are strongly avoided in fermentation strains. Therefore, beta-galactosidase-deficient stains were applied in the fermentation (see, e.g. Dumon et al., (2004) Biotechnol. Prog. 20, 412-419) or the beta-galactosidase gene of the strain has been specifically inactivated (Dumon et al., (2006) Chem Bio Chem. 7, 359-365)). Generally, the presences of any glycosidase activity are seen as contra productive to the fermentation of oligosaccharides.

According to the invention, an "oligosaccharide" is to be understood to be short polymers of monosaccharides, comprising at least 2 sugar-subunits, as already mentioned at the outset. The oligosaccharides may either be branched or form a linear chain of subunits. Moreover, the sugar subunits of oligosaccharides may feature a number of chemical modifications. Accordingly, the oligosaccharides according to the present invention may comprise one or more non-sugar moieties.

Also, presently and generally in the relevant field, a "glycosidase"—also designated as "glycoside hydrolases" or "glycosyl hydrolases" catalyze the hydrolysis of the glycosidic linkage to release smaller sugars. They can be classified as enzymes catalyzing the hydrolysis of O- or S-glycosides, and they are typically named after the substrate that they act upon. Accordingly, glucosidases catalyze the hydrolysis of glucosides and xylanases catalyze the cleavage of xylan. Thus, a glycosidase according to the invention catalyses the hydrolysis of glycosidic bonds to liberate monosaccharides and oligosaccharides of lower molecular weight than the native simple as well complex carbohydrate substrates.

According to the invention, in the use and the processes disclosed herein a gloycosidase is employed to degrade hindering and/or undesired side-products, unused starting substrates and intermediate products generated during the production of the desired oligosaccharide which undesired side-products, unused starting substrates and intermediate products generally have a higher molecular weight compared to the monosaccharides and oligo- or disaccharides liberated by the action of the glycosidase during degradation of the undesired side-products, unused starting substrates and intermediate products.

Thus, presently, a "liberated monosaccharide" is to be understood as a monosaccharide that has been generated during the glycosidase-mediated hydrolysis of a glycosidic bond of a carbohydrate substrate where monosaccharides and oligosaccharides of lower molecular weight than the hydrolyzed carbohydrate substrate are formed.

According to the invention, at least one glycosidase, or a combination of two or more may be applied in the use and the process according to the invention.

According to one aspect of the invention, the glycosidase is used in a microbial fermentation process employed for the production of the desired oligosaccharide and using a host microorganism, wherein said oligosaccharide and/or said glycosidase are not naturally occurring in the microorganism to said host cell.

Presently and as generally understood in the related field, a "microbial fermentation" is to be understood as a—generally large-scale—industrial metabolic process where during cultivation of microorganisms such as bacteria, fungi and moulds, enzymatic decomposition and utililization of nutrients, particularly carbohydrates, and the conversion of compounds into other compounds takes place. As such, industrial or large-scale microbial fermentation is the process of controlling microorganisms, i.e. bacteria, yeast, and moulds, to modify food, producing a desired product.

According to another aspect of the invention, the glycosidase is used for resolution of oligosaccharide mixtures obtained by in vitro oligosaccharide synthesis reactions or by chemical synthesis or by combinations thereof.

Presently, and generally in the relevant field, a "microorganism" presently designates and encompasses any microscopic organism that comprises either a single cell, cell clusters, or multicellular relatively complex organisms, which is suitable to be employed in the process according to the invention, and particularly includes bacteria and yeast. A microorganism as employed according to the invention can be cultivated in a liquid medium, and generally needs a carbon source in the medium to grow and replicate.

Presently, and throughout the invention, "recombinant" means genetically engineered DNA prepared by transplanting or splicing genes from one species into the cells of a host microorganism of a different species. Such DNA becomes part of the host's genetic makeup and is replicated.

Consequently, "a host microorganism" is designated to mean any microorganism containing nucleic acid sequences or expressed proteins foreign to/not naturally occurring in the thus recombinant host microorganism and wherein the foreign/not naturally in said microorganism occurring nucleic acid sequence is integrated in the genome of the host microorganism cell. Thereby, "not naturally occurring" means that the nucleic acid sequence/protein (such as, e.g. an enzyme), is foreign to said host microorganism cell, i.e. the nucleic acid sequences/proteins are heterologous with respect to the microorganism host cell. The heterologous sequence may be stably introduced, e.g. by transfection, transformation, or transduction, into the genome of the host microorganism cell, wherein techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989). Thus, the host microorganism the heterologous sequence has been introduced in will produce the heterologous proteins the nucleic acid sequences according to the invention are coding for.

For recombinant production, host cells can be genetically engineered to incorporate expression systems or portions thereof and the nucleic acid sequences of the invention. Introduction of a nucleic acid sequence into the host microorganism cell can be effected by methods described in many standard laboratory manuals, such as Davis et al., Basic Methods in Molecular Biology, (1986), and Sambrook et al., 1989, supra.

Thus, the nucleic acid sequences according to the invention, may, e.g., be comprised in a vector which is to be stably transformed/transfected or otherwise introduced into host microorganism cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesize a polypeptide in a host may be used for expression in this regard. The appropriate DNA sequence may be inserted into the expression system by any of a variety of well-known and routine techniques, such as, for example, those set forth in Sambrook et al., supra.

Presently, a "desired oligosaccharide" designates an oligosaccharide that shall specifically and intentionally be produced with the applied process. Accordingly, a "non-desired oligosaccharide" represents an oligosaccharide not intended to be produced or generated during the production of the desired oligosaccharide or an oligosaccharide formed by the used organism unrelated to the desired oligosaccharide. A "metabolic product" or "metabolic" saccharide product" or "saccharide intermediate" is a saccharide, i.e. carbohydrate product generated during production of a desired oligosaccharide, and an "unused saccharide substrate" represents a starting molecule or moiety used for/during the production of the desired oligosaccharide.

As mentioned at the outset, the invention also relates to a process for producing an oligosaccharide using a host microorganism, wherein said oligosaccharide is not naturally occurring in said host cell, the process comprising the steps of a) cultivating a host microorganism suitable for the production of a desired oligosaccharide under conditions and in a medium permissive for the production of said oligosaccharide, whereby the oligosaccharide and, where applicable, biosynthetic saccharide intermediates and/or saccharide side products are produced; b) using a glycosidase in the medium the host microorganism is cultivated in, in order to degrade biosynthetic intermediates and/or side products and/or unused substrates, and c) recovering the desired oligosaccharide.

With the process according to the invention, an effective manufacturing method has been provided, by means of which a desired oligosaccharide can be produced in a form where non-desired oligosaccharides or otherwise hindering intermediate products or unused substrates are essentially no longer present.

As used herein, the term "cultivating" means growing a microorganism in a medium and under conditions permissive and suitable for the production of the desired oligosaccharide. A couple of suitable host microorganisms as well as the mediums and conditions for their cultivation will be readily available for one skilled in the art upon reading the disclosure of this invention in connection with the skilled person's technical and expert background.

As used herein, the term "recovering" means isolating, harvesting, purifying, collecting or otherwise separating from the host microorganism culture the oligosaccharide produced by the host microorganism according to the invention.

According to one aspect of the invention, the glycosidase is added to the medium the microorganism is cultivated in. "Adding" hereby means the direct addition of the enzyme to the medium, i.e. contrary to a provision of the glycosidase that would be endogenously produced by the microorganism used for the production. As such, the enzyme is—in its active form—readily and commercially available on the market and can be added in amounts necessary to degrade the undesired oligosaccharides/unused substrates/intermediates. The amount to be applied will depend from the amount of the cultivated microorganism and also from amount of the produced desired oligosaccharide, the amount of substrate and likely to be expected intermediates.

The glycosidase(s) are, according to this embodiment, externally added to the medium/the supernatant at the end of the production process according to the invention, which is particularly preferred when endogenous genes of the host microorganism encoding glycosidases have been inactivated or deleted. In doing so, undesired oligo- and or monosaccharides cannot accumulate and do not interfere with the recovering of the desired oligosaccharide.

E.g., to a solution containing a desired oligosaccharide and a non-desired oligosaccharide, such as fermentation derived lacto-N-tetraose and lactose, beta-galactosidase is added; the amount of beta-galactosidase to be employed will depend on the (actual or expected) amount of oligosaccharides. E.g. with lacto-N-tetraose and lactose both at 10 mM concentration an amount of 50 units/ml (final concentration) of beta-galactosidase (e.g. from Sigma-Aldrich Chemie GmbH, Munich Germany catalog No. G6008)) can achieve good results in order to cleave the lactose in glucose and galactose for better chromatographic separation of the saccharides (e.g. by size dependent gel-filtration chromatography). In respective experiments conducted by the inventors, it could be shown that within seconds the lactose was cleaved into its monosaccharides galactose and glucose, whereas the lacto-N-tetraose remained as such (see also FIG. 1 and the respective description below). These experiments proved the highly selective action of the purified E. coli beta-galactosidase, which selectively only hydrolyzes the Gal(beta1-4)Glc glycosidic bond and not the Gal(beta1-3) GlcNAc glycosidic bond present at the non-reducing end of the lacto-N-tetraose. It will be apparent from the present disclosure how much of the respective glycosidase is likely needed to be used.

E.g., suitable microorganisms for producing, e.g., fucosylated oligosaccharides in fermentation proceedings are known from EP 2 479 263 A1 or from EP 2 439 264 or from WO 2010/142305, the content of which is herewith explicitly referred to and made subject matter of this invention.

According to another aspect of the invention, the glycosidase is endogenously produced by said host microorganism, wherein the nucleic acid sequences encod-ing the endogenously produced glycosidase is not naturally occurring in said host cell, and wherein said host cell has been stably transformed to express the not naturally occurring glycosidase, and wherein the expression of the glycosidase in the host microorganism is inducable.

According to this embodiment, the oligosaccharide producing microorganism endogenously, i.e. contained in its genome, expresses the glycosidase, e.g. beta-galactosidase, upon external induction, e.g., via temperature or substrate-induced expression, which is otherwise deregulated. This means that during synthesis of the desired oligosaccharide, the glycosidase is deregulated and may be induced, e.g. by temperature or adding a inductor, e.g. tetracyclin, at the end of the fermentation process. The expression of the glycosidase will be induced after a sufficient and/or essentially maximum amount of oligosaccharide has been produced during cultivation of the host microorganism. Subsequently, the expressed glycosidase will degrade undesired saccharide intermediates, substrates, etc., rendering the medium essentially free of the saccharide intermediates or substrates that would otherwise hinder or complicate the purification of the desired oligosaccharide. A couple of suitable inducable expression tools are known in the prior art (see, e.g. Sambrook et. al, 1989, supra), and one skilled will be able to apply a respectively suitable one for the desired oligosaccharide.

"Regulated" within the present context with reference to a gene is generally understood as a gene, whose expression can be regulated in a controlled fashion, e.g. down- or up-regulated, i.e. the quantity of the synthesised protein encoded by the regulated gene is different, e.g. de-/down-regulated or upregulated, from the otherwise unregulated gene.

According to another aspect of the invention, the glycosidase is produced by a second microorganism additionally added to the medium and expressing the glycosidase.

In this embodiment, the glycosidase expressed by the microorganism is either a naturally occurring glycosidase or a glycosidase that is encoded by a nucleic acid sequence that has been stably integrated into the genome of the second microorganism. This embodiment is particularly suitable in a continuous fermentation process for the production of the oligosaccharide, where, e.g., two separate fermentation vessels or containers are provided, whereas one vessel/container is used for the oligosaccharide synthesis reaction and the second vessel/container is essentially employed for the degradation of undesired saccharides.

Accordingly, and according to certain aspects of the invention, the process according to the invention is a batch or a continuous process.

Thus, according to one aspect of the invention, i.e. in a continuous process, the glycosidase is constantly added to the medium during the cultivating step of the host microorganism, e.g. by the provision of a strain expressing a glycosidase, whereas the glycosidic and catabolic reactions can be spatially separated.

According to another aspect, i.e. in a batch or feed-batch process, the hydrolytic cleavage reactions are restricted to particular periods.

According to another aspect of the invention, the oligosaccharide is recovered from supernatant of the cultivated host microorganism, which supernatant is obtained by centrifuging the cultivated host microorganism to obtain a supernatant and a host microorganism pellet.

With the newly provided process, it is possible to retrieve the produced oligosaccharide from the medium the host microorganism is cultivated in, since the oligosaccharide which is produced in a microorganism cell is preferably transported into the medium, thus making it effortlessly possible to recover the oligosaccharide from the supernatant, once the cells of the microorganism have been separated from the cultivation medium.

Also, according to another aspect of the invention, prior to the adding of the glycosidase, a supernatant may be produced separating the host microorganisms from the preferably liquid medium the host microorganism is cultivated in, wherein the produced oligosaccharide is contained in the supernatant. To this supernatant, the glycosidase may be added.

According to another aspect, the desired oligosaccharide is selected from 2'-fucosyllactose (2'-FL), 3-fucosyllactose (3-FL), difucosyllactose (DF-L), 3'-sialyllactose (3'-SL), 6'-sialyllactose (6'-SL), 3-fucosyl-3'-sialyllactose (F-SL), lacto-N-tetraose ((LNT), lacto-N-neotetraose (LNneoT), lacto-N-fucopentaose(s) (LNFP-I, II, III, V), lacto-N-difucohexaose(s) (LNDH-I and II), lacto-N-sialylpentaose(s) (LSTa, b and c), fucosyl-lacto-N-sialylhexaose (F-LSTa, b and c), disialyl-lacto-N-hexaose (DS-LNT) and in particularly selected from those shown in table 1, or derivatives thereof. In this regard, for the production of the oligosaccharides, it is explicitly referred to EP 2 479 263 A1 or from EP 2 439 264 or from WO 2010/142305, the content of which is herewith explicitly referred to and made subject matter of this invention.

TABLE 1 list of oligosaccharides that can be produced according to the invention (Fig. 11)

| No. | Name | Abbreviation | Oligosaccharide |
|---|---|---|---|
| 1 | 2'-Fucosyllactose | 2'-FL | Fuc($\alpha$1-2)Gal($\beta$1-4)Gluc |
| 2 | 3-Fucosyllactose | 3-FL | Gal($\beta$1-4)Gluc<br>        |<br>Fuc($\alpha$1-3) |
| 3 | 2',3-Difucosyllactose | DF-L | Fuc($\alpha$1-2)Gal($\beta$1-4)Gluc<br>                      |<br>Fuc($\alpha$1-3) |
| 5 | Lacto-N-triose II | LNT II | GlcNAc($\beta$1-3)Gal($\beta$1-4)Gluc |
| 6 | Lacto-N-tetraose | LNT | Gal($\beta$1-3)GlcNAc($\beta$1-3)Gal($\beta$1-4)Gluc |
| 7 | Lacto-N-neotetraose | LNnT | Gal($\beta$1-4)GlcNAc($\beta$1-3)Gal($\beta$1-4)Gluc |
| 8 | Lacto-N-fucopentaose I | LNFP I | Fuc($\alpha$1-2)Gal($\beta$1-3)GcNAc($\beta$1-3)Gal($\beta$1-4)Gluc |
| 9 | Lacto-N-neofucopentaose I | LNnFP I | Fuc($\alpha$1-2)Gal($\beta$1-4)GlcNAc($\beta$1-3)Gal($\beta$1-4)Gluc |
| 10 | Lacto-N-fucopentaose II | LNFP II | Gal($\beta$1-3)GlcNAc($\beta$1-3)Gal($\beta$1-4)Gluc<br>           |<br>Fuc($\alpha$1-4) |
| 11 | Lacto-N-fucopentaose III | LNFP III | Gal($\beta$1-4)GlcNAc($\beta$1-3)Gal($\beta$1-4)Gluc<br>           |<br>Fuc($\alpha$1-3) |
| 12 | Lacto-N-fucopentaose V | LNFP V | Gal($\beta$1-3)GlcNAc($\beta$1-3)Gal($\beta$1-4)Gluc<br>                                |<br>Fuc($\alpha$1-3) |
| 13 | Lacto-N-neofucopentaose V | LNnFP V | Gal($\beta$1-4)GlcNAc($\beta$1-3)Gal($\beta$1-4)Gluc<br>                                |<br>Fuc($\alpha$1-3) |
| 14 | Lacto-N-thfucohexaose I | LNDH I | Gal($\beta$1-3)GlcNAc($\beta$1-3)Gal($\beta$1-4)Gluc<br>       |           |<br>Fuc($\alpha$1-2)  Fuc($\alpha$1-4) |
| 15 | Lacto-N-difilcohexaose II | LND | Gal($\beta$1-3)GlcNAc($\beta$1-3)Gal($\beta$1-4)Gluc<br>       |                    |<br>Fuc($\alpha$1-4)       Fuc($\alpha$1-3) |

TABLE 1-continued list of oligosaccharides that can be produced according to the invention (Fig. 11)

| No. | Name | Abbreviation | Oligosaccharide |
|---|---|---|---|
| 16 | 6'-Galactosyllactose | 6'-GL | Gal(β1-6)Gal(β1-4)Gluc |
| 17 | 3'-Galactosyllactose | 3'-GL | Gal(β1-3)Gal(β1-4)Gluc |
| 18 | Lacto-N-hexaose | LNH | Gal(β1-4)GlcNAc(β1-6)Gal(β1-4)Gluc<br>\|<br>Gal(β1-3)GlcNAc(β1-3) |
| 19 | Lacto-N-neohexaose | LNnH | Gal(β1-4)GlcNAc(β1-6)Gal(β1-4)Gluc<br>\|<br>Gal(β1-4)GlcNAc(β1-3) |
| 20 | para-Lacto-N-hexaose | paraLNT | Gal(β1-3)GlcNAc(β1-3)Gal(β1-4)GlcNAc(β1-3)Gal(β1-4)Gluc |
| 21 | para-Lacto-N-neohexaose | paraLNnH | Gal(β1-4)GlcNAc(β1-3)Gal(β1-4)GlcNAc(β1-3)Gal(β1-4)Gluc |
| 22 | Difucosyl-lacto-N-neohexaose | DF-LNnH | Fuc(α1-3)<br>\|<br>Gal(β1-4)GlcNAc(β1-6)Gal(β1-4)Glc<br>\|<br>Gal(β1-4)GlcNAc(β1-3)<br>\|<br>Fuc(α1-3) |
| 23 | 3'-Sialyllactose | 3'-SL | Neu5Ac(α2-3)Gal(β1-4)Gluc |
| 24 | 6'-Sialyllactose | 6'-SL | Neu5Ac(α2-6)Gal(β1-4)Gluc |
| 25 | Lacto-N-sialylpentaose a | LST-a | Neu5Ac(α2-3)Gal(β1-3)GlcNAc(β1-3)Gal(β1-4)Gluc |
| 26 | Lacto-N-sialylpentaose b | LST-b | Gal(β1-3)GlcNAc(β1-3)Gal(β1-4)Gluc<br>\|<br>Neu5Ac(α2-6) |
| 27 | Lacto-N-sialylpentaose c | LST-c | Neu5Ac(α2-6)Gal(β1-4)GlcNAc(β1-3)Gal(β1-4)Gluc |
| 28 | Fucosyl-lacto-N-sialylpentaose a | F-LST-a | Neu5Ac(α2-3)Gal(β1-3)GlcNAc(β1-3)Gal(β1-4)Gluc<br>\|<br>Fuc(α1-4) |
| 29 | Fucosyl-lacto-N-sialylpentaose b | F-LST-b | Fuc(α1-2)Gal(β1-3)GlcNAc(β1-3)Gal(β1-4)Gluc<br>\|<br>Neu5Ac(α2-6) |
| 30 | Fucosyl-lacto-N-sialylpentaose c | F-LST-c | Neu5Ac(α2-3)Gal(β1-3)GlcNAc(β1-3)Gal(β1-4)Gluc<br>\|<br>Fuc(α1-3) |
| 31 | Disialyl-lacto-N-tetraose | DS-LNT | Neu5Ac(α2-3)Gal(β1-4)GlcNAc(β1-3)Gal(β1-4)Gluc<br>\|<br>Neu5Ac(α2-6) |
| 32 | Disialyl-lacto-N-fucopentaose | DS-LNFP V | Neu5Ac(α2-3)Gal(β1-4)GlcNAc(β1-3)Gal(β1-4)Gluc<br>\|              \|<br>Neu5Ac(α2-6)     Fuc(α1-3) |
| 33 | 3-Fucosyl-3'-sialyllactose | 3F-3'-SL | Neu5Ac(α2-3)Gal(β1-4)Gluc<br>\|<br>Fuc(α1-3) |
| 34 | 3-Fucosyl-6'-sialyllactose | 3F-6'-SL | Neu5Ac(α2-6)Gal(β1-4)Gluc<br>\|<br>Fuc(α1-3) |
| 35 | Lacto-N-neodifucohexaose I | LNnDFH I | Gal(β1-4)GalNAc(β1-3)Gal(β1-4)Glc<br>\|              \|<br>Fuc(α1-3)     Fuc(α1-3) |

According to another aspect of the invention, in the process according to the invention or in the use according to the invention, the glycosidase is selected from one or more of the group comprising galactosidases, glucosidases, galactosidases, N-acetyl-glucosamidases, N-acetyl-hexoamidases, mannosidases, fucosidases and sialidases, which also sometimes also referred to as neuraminidases.

In this regard, it is preferred if the glycosidase is selected from one or more of the group comprising beta-galactosidase, beta-glucosidase, beta-N-acetylhexoamidase, alpha-fucosidase, beta-fucosidase, alpha-glucosidase alpha-galactosidase, beta-mannosidase, alpha-mannosidase, neuramidase, and it is particularly preferred if the glycosidase is a beta-galactosidase, preferably an *E. coli* beta-galactosidase.

"Beta-galactosidase" as it is used herein and as generally understood within the field of the invention, is a hydrolase enzyme that catalyzes the hydrolysis of beta-galactosides into monosaccharides.

Beta-galactosidases, are regularly employed in the genetics, molecular biology and biotechnical engineering techniques, and are per se known to one skilled in the art.

According to a preferred embodiment, the microorganism—used in the process according to the invention and claimed therein—is selected from a bacterium or a yeast, and more preferably, the host microorganism is an *Escherichia coli* strain, a *Corynebacterium* strain, in particular *Corynebacterium glutamicum*, a *Lactobacillus* species, or a *Saccharomyces* sp. strain.

The bacteria *Escherichia coli, Lactobacillus* sp., and *Corynebacterium glutamicum* and the yeast *Saccharomyces* sp. have the advantage that these microorganisms can be grown easily and inexpensively in laboratory settings, and the bacteria and yeast have been intensively investigated for over 60 years.

Accordingly, in a preferred embodiment, the host microorganism used in the process according to the invention and otherwise claimed therein is selected from the group consisting of bacteria and yeast, and is preferably an *Escherichia coli* strain.

According to another aspect of the invention, in the process or the use according to the invention, the host microorganism employed, and preferably expressing a glycosidase, is further expressing proteins for sugar catabolic pathways otherwise not present in the microorganism, which proteins are selected from at least one of the following: galactose catabolic pathway proteins, such as encoded by the gal operon when using a galcatosidase, fucose catabolic pathway when using a fucosidase, N-acetylglucosamine catabolic pathway using beta-N-acetylhexosaminidase. By using the beta-N-acetylhexosaminidase for the degradation of terminal N-acetylglucosamine containing oligosaccharides it proved beneficial to overexpress enzymes involved in the catabolism of the monosaccharide N-acetylglucosamine. Likewise, if the liberated monosaccharide is L-fucose, it is advantageous to express the L-fucose catabolic pathway. Same holds true for sialic acid etc.

This embodiment has the advantage that with the deregulation of sugar catabolic pathways the monosaccharides liberated by the action of the glycosidases can be efficiently and effectively removed from the fermentation medium. Alternatively, also monosaccharides added as precursors can be equally removed from the fermentation medium by this means. Thus, the host microorganism expresses, besides the glycosidase, proteins for sugar catabolic pathways, such as the galactose catabolic pathway, in order to prevent the accumulation of the degradation product galactose. However, the glycosidase and the sugar catabolic pathway do not have to be expressed by an individual organism, they can be also expressed by two different co-cultured strains or the glycosidase(s) is added to a suitable strain capable of the desired monosaccharide catabolism.

According to another embodiment, and alternatively to expressing a sugar catabolic pathway for the liberated monosaccharide, the monosaccharide liberated during degradation of the undesired side-products, unused starting substrates and intermediate products can be conferred into its nucleotide activated form by expressing its salvage pathway and reused for oligosaccharide synthesis. Thus, e.g. Fucose can be conferred into GDP-Fucose, or sialic acid into CMP-Neu5Ac.

E.g., if fucose is generated as liberated monosaccharide, its salvage pathway can be used (i.e. overexpressed (highly regulated) in the host microorganism fucose has been generated) to confer the fucose into GDP-fucose.

In the so called "fucose salvage pathway" fucose is first phosphorylated to fucose-1-phosphate by the enzyme fucose kinase. The fucose-1-phosphate is then converted to GDP-fucose by the action of the enzyme fucose-1-P-guanylyltransferase. Thus, according to one aspect, a microorganism can be employed which is genetically modified to express a fucose kinase and a guanylyltransferase. According to one embodiment, the bacterial enzyme Fkp is used which represents the first identified bifunctional enzyme with both fucose kinase and L-fucose-1-P-guanylyltransferase. A detailed description of generating such genetically modified microorganisms can found in WO 2010/070104 A1, the disclosure of which is explicitly referred to and whose content is explicitly incorporated by reference.

For the fermentation of more complex oligosaccharides the combination of glycosidases is employed, i.e. expressed in the host microorganism, such as beta-galactosidase and a beta-N-acetylhexosaminidase, the latter of which specifically degrades lacto-N-triose II (LNT-2) into N-acetylglucosamine and lactose. The released N-acetylglucosamine and galactosamine can then equally efficient removed from the fermentation medium by deregulating or introducing specific monosaccharide importers and the monosaccharide specific catabolic pathway.

According to another embodiment of the process and use of the invention, the host microorganism to be employed is wild-type expressing proteins for sugar catabolic pathways, which proteins are selected from at least one of the following: galactose catabolic pathway proteins when using a galcatosidase, fucose catabolic pathway when using a fucosidase, N-acetylglucosamine catabolic pathway using beta-N-acetylhexosaminidase, sialic acid, wherein an overerexpression of such proteins is induced in said host microorganism during the process or the use.

This embodiment has the advantage that a host microorganism already comprising and expressing the desired proteins for the sugar catabolic pathways, can be employed, wherein the overexpression of such protein(s) is induced. The overexpression can be achieved, e.g., by putting the nucleic acid sequence coding for these proteins under control of an inducible promoter, so that the expression of the gene/polynucleotide can be specifically targeted, and, overexpressed in that way.

The expression system constructs thus contain control regions that regulate as well as engender expression. Generally, any system or vector suitable to maintain, propagate or express proteins and/or to express a protein in a host may be used for expression in this regard. The appropriate DNA sequence may be inserted into the expression system by any of a variety of well-known and routine techniques, such as, for example, those set forth in Sambrook et al., see above.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described above and below are those well known and commonly employed in the art.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

Description of Preferred Embodiments

To a solution containing fermentation derived lacto-N-tetraose and lactose, both at 10 mM concentration, beta-galactosidase was added; 50 units/ml (final concentration) of beta-galactosidase (Sigma-Aldrich Chemie GmbH, Munich Germany catalog No. G6008)) were added in order to cleave the lactose in glucose and galactose for better chromatographic separation of the saccharides (e.g. by size dependent gel-filtration chromatography). It could be shown that within seconds the lactose was cleaved into its monosaccharides galactose and glucose, whereas the lacto-N-tetraose remained as such (see also FIG. 1). These experiments proved the highly selective action of the purified *E. coli* beta-galactosidase, which selectively only hydrolyzes the Gal(beta1-4)Glc glycosidic bond and not the Gal(beta1-3) GlcNAc glycosidic bond present at the non-reducing end of the lacto-N-tetraose. Accordingly, FIG. 1A shows the superimposed HPLC chromatograms of 10 mM lactose and 10 mM lacto-N-tetraose (authentic standards), and FIG. 1B shows the HPLC chromatogram of beta-galactosidase reaction containing 10 mM lactose and 10 mM lacto-N-tetraose immediately taken after enzyme addition. FIG. 1C shows the HPLC chromatogram of the beta-galactosidase reaction containing 10 mM lactose and 10 mM lacto-N-tetraose taken 3 hours post enzyme addition.

Figure 2:
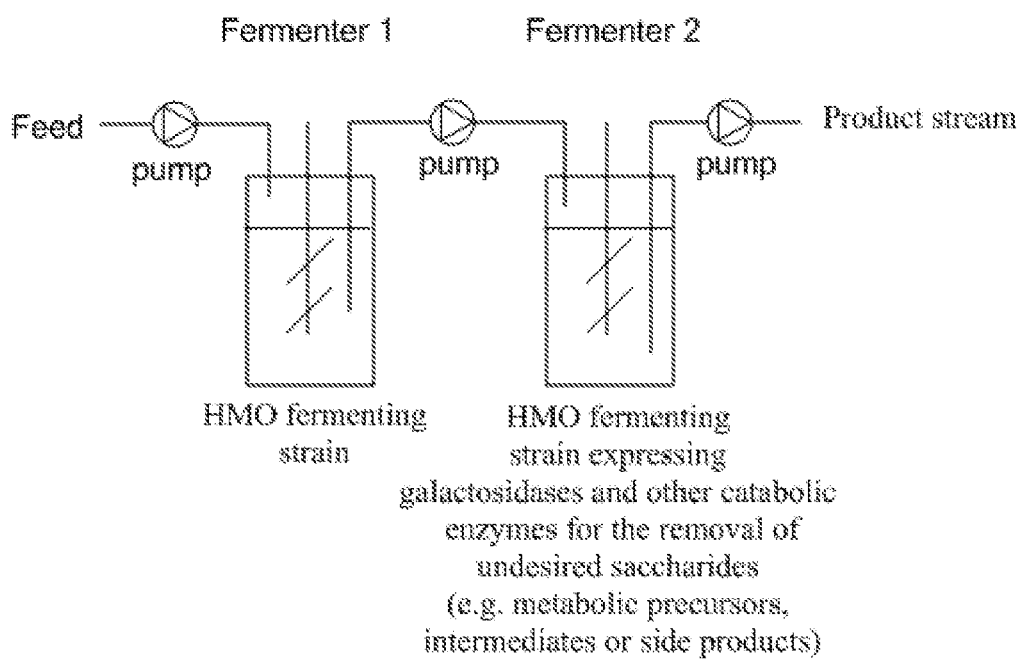
FIG. 2 shows a diagram displaying a continuous fermentation set-up suitable for the production of an oligosaccharide, such as 2'-fucosyllactose, 3-fucosyllactose, 2'3-difucosyllactose, 3'-sialyllactose, 6'-sialyllactose, according to one embodiment of the invention, with a first fermenter and a second fermenter.

FIG. 2 shows a continuous fermentation set-up useful for the production of oligosaccharides such as 2'-fucosyllactose, 3-fucosyllactose, 2',3-difucosyllactose, 3'-sialyllactose or 6'-sialyllactose and derivatives thereof, according to one embodiment of the invention.

The first fermenter vessel ("Fermenter 1") is used for the continuous synthesis of the desired oligosaccharide whereas the second fermentation vessel ("Fermenter 2") containing a microbial strain expressing a suitable glycosidase, such as beta-galactosidase, is used for the degradation of excess monosaccharides, such as lactose and other saccharides present in the medium interfering with the subsequent purification of the desired oligosaccharide product. Fermenter 1 and Fermenter 2 are connected with each other suitable conduits and a pump effects the transferral of the fermentation slurry from Fermenter 1 to Fermenter 2. Another pump removes the stream containing the desired oligosaccharide product from Fermenter 2.

Resolution of Saccharide Mixtures by Glycosidase Treatment in the Production of 2'-fucosyllactose A 2'-fucosyllactose feed-batch fermentation employing a recombinant 2'-fucosyllactose synthesizing *E. coli* strain (*E. coli* BL21(DE3) ΔlacZ, containing a genomic integration 2'-fuosyltranferase, encoded by the wbgL gene (EP 11 1151 571.4), and having an additional copy of the *E. coli* lacY, manB, manC, gmd and fcl all under the control of an strong constitutive tetracyclin promoter, containing a functional gal operon comprising the gens galM, galK, galT and galE; see FIG. 10; forward primer P-TTACTCAGCAATAAACTGA-TATTCCGTCAGGCTGG (SEQ ID No. 2); reverse primer P-TTGATAATCTCGCGCTCTTCAGCAGTCAGACT-TTCCATATAGAGCGTAATTTCCG TTAACGTCGGT-AGTGCTGACCTTGCCGGAGG (SEQ ID. No. 3)) grown in a defined salt medium (7 g l$^{-1}$ NH$_4$H$_2$PO$_4$, 7 g l$^{-1}$ K$_2$HPO$_4$, 2 g l$^{-1}$ KOH, 0.37 g l$^{-1}$ citric acid, 1 ml l$^{-1}$ antifoam (Struktol J673, Schill+Seilacher), 1 mM CaCl$_2$, 4 mM MgSO$_4$, Trace-Elements consisted of 0.101 g l$^{-1}$ nitrilotriacetic acid pH 6.5, 0.056 g l$^{-1}$ ammonium ferric citrate, 0.01 g l$^{-1}$ MnCl$_2$×4 H$_2$O, 0.002 g l$^{-1}$ CoCl$_2$×6 H$_2$O, 0.001 g l$^{-1}$ CuCl$_2$×2 H$_2$O, 0.002 g l$^{-1}$ boric acid, 0.009 g l$^{-1}$ ZnSO$_4$×7 H$_2$O, 0.001 g l$^{-1}$ Na$_2$MoO$_4$×2 H$_2$O, 0.002 g l$^{-1}$ Na$_2$SeO$_3$, 0.002 g l$^{-1}$ NiSO$_4$×6 H$_2$O with 2% glycerol as carbon source); Glycerol-feed consisted of glycerol 800 g l$^{-1}$, MgSO$_4$ 2.64 g l$^{-1}$ and trace element solution 4 ml l$^{-1}$. For 2'-fucosyllactose formation a lactose feed of 216 g l$^{-1}$ was employed. The pH was controlled by using ammonia solution (25% v/v), which also served as a nitrogen-source. Lactose was supplied as a precursor for the 2'-fucosyllactose production. Feed batch was cultured at 30° C. under constant aeration and agitation for 90 hours. At 90 hours after the start of the fermentation most of the added lactose was converted into 2'-fucosyllactose.

In order to remove most or all lactose still present in the fermentation supernatant, a second bacterial strain was added to the fermentation vessel 90 hour post fermentation start (see set-up in FIG. 2). The added second bacterial strain was genetically identical to the first employed bacteria strain, differing, however, only in the expression of a genome integrated beta-galactosidase and expressing a functional gal operon (see FIG. 10) (for D-galactose degradation). Incubation of the added secondary bacterial strain resulted in the disappearance of the residual lactose within 5 hours. Approximately 25 ml starter culture of the second beta-galactosidase expressing bacterial strain was added per 1l fermentation broth.

Figure 3:
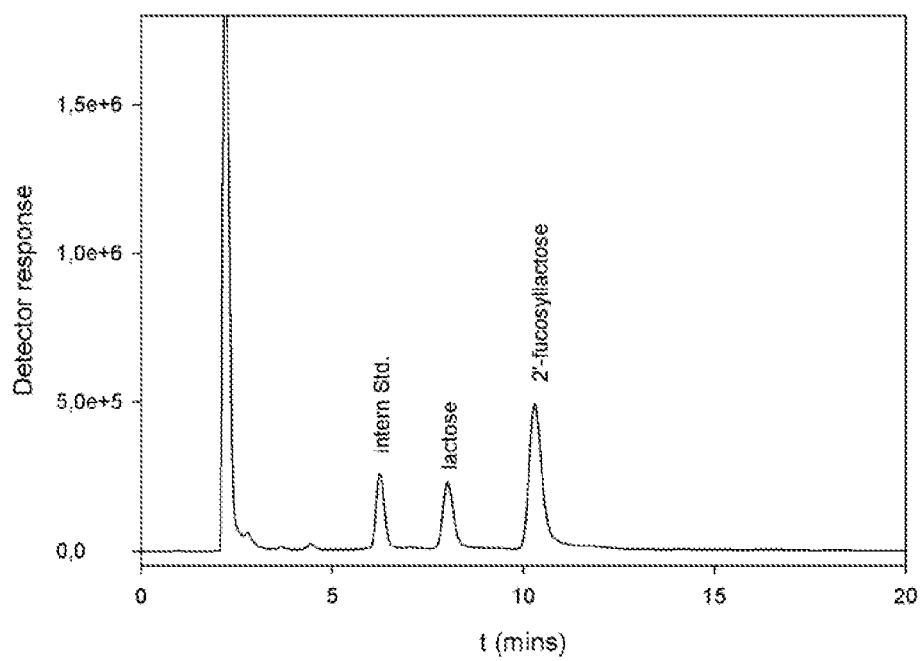
FIG. 3 shows a HPLC analysis of a cell free medium sample prior to the addition of a beta-galactosidase expressing E. coli strain to the fermentation. The strain also expressed the galactose catabolic pathway in order to prevent galactose accumulation.
Figure 4:
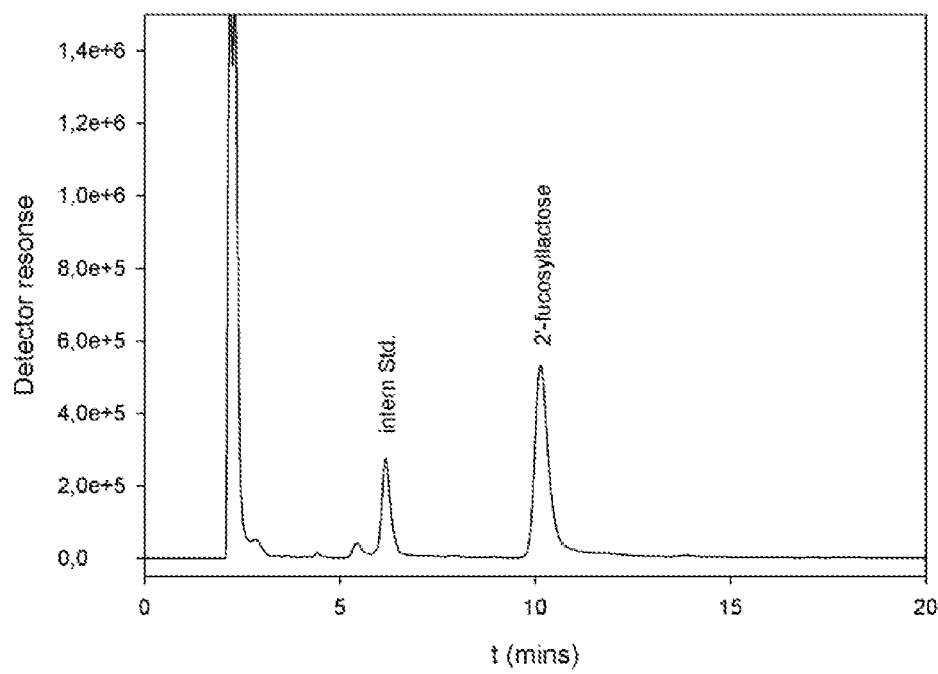
FIG. 4 shows a HPLC analysis of a cell free medium sample post addition of a second beta-galactosidase expressing E. coli strain to the fermentation.

For the HPLC analysis, a cell free sterile filtered medium sample was used, and desalted by passing a 350 µl sample over a desalting column (Strata ABW (55 µm, 70 A) phenomenex, Aschaffenburg, Germany). For HPLC analysis, a ReproSil Carbohydrate 5 µm, 250×4.6 mm column (Dr. Maisch GmbH, Ammerbuch-Entringen, Germany) was used with the following conditions: eluent acetonitrile/ddH$_2$O (68:32), isocratic condition with flow rate of 1.4 ml/min (column oven was set to 35° C.); as an internal standard for quantification sucrose was used; for identification of lactose and 2'-fucosyllactose authentic standards were employed. For the detection a refractive index detector (RID) was employed. The inclusion of the glycosidase resolution step at the end of the fermentative process led to a significant reduction in the complexity of the resulting fermentation filtrate. FIG. 3 shows the analysis of cell free fermentation medium taken before glycosidase treatment and FIG. 4 shows a sample taken after glycosidase treatment: The comparison of the HPLC chromatograms clearly shows the disappearance of the lactose present in the sample before beta-galactosidase treatment. The strain also expressed the galactose catabolic pathway in order to prevent D-galactose accumulation.

Figure 5:
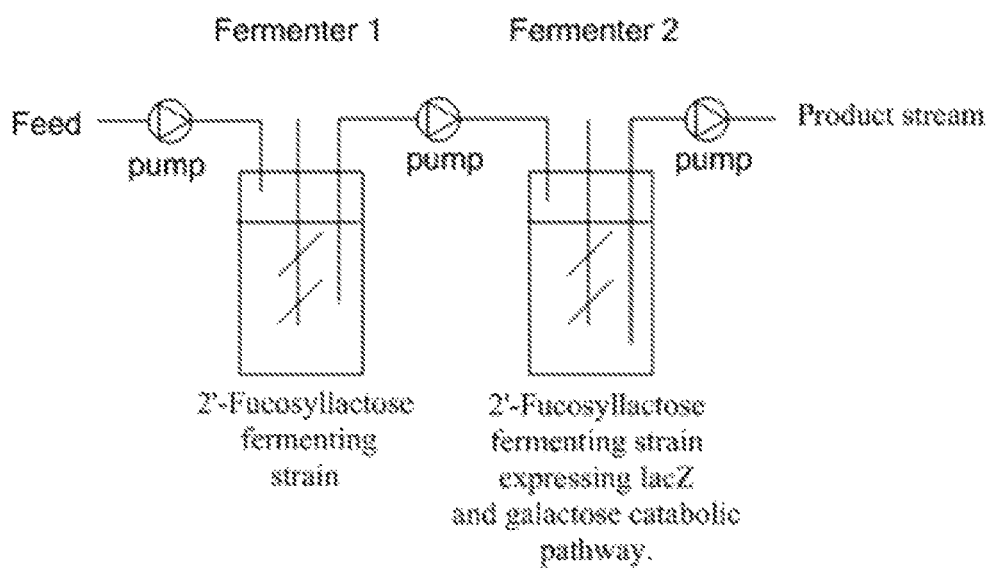
FIG. 5 shows a diagram displaying a continuous fermentation set-up useful for the production of 2'-fucosyllactose according to one embodiment of the invention. The first fermenter vessel is used for the continuous synthesis of the synthesis of 2'-fucosyl-lactose whereas the second fermentation vessel besides the synthesis of 2'fucosyllactose is employed for the removal of excess substrate (lactose) and other saccharide side products.

Resolution of Saccharide Mixtures by Glycosidase Treatment in the Continuous Production of 2'-fucosyllactose Continuous synthesis of 2'-Fucosyllactose was achieved by using two fermentation vessels, fermenter 1 containing a 2'-fucosyllactose fermenting strain deficient in lactose degradation (*E. coli* BL21(DE3) ΔlacZ, containing a genomic integration 2'-fuosyltranferase, encoded by the wbgL gene (EP 11 1151 571.4), and having an additional copy of the *E. coli* lacY, manB, manC, gmd and fcl all under the control of an strong constitutive tetracyclin promoter, containing a functional gal operon (see FIG. 10) comprising the gens galM, galK, galT and galE). Fermenter 2 contained a starter culture genetically similar to the used 2'-fucosyllactose fermenting strain of fermenter 1 except that this strain expressed in addition the *E. coli* lacZ gene encoding a beta-galactosidase (see set-up displayed in FIG. 5). For both fermenters a defined salt medium containing 7 g $l^{-1}$ $NH_4H_3PO_4$, 7 g $l^{-1}$ $K_2HPO_4$, 2 g $l^{-1}$ KOH, 0.37 g $l^{-1}$ citric acid, 1 ml $l^{-1}$ antifoam (Struktol J673, Schill+Seilacher), 1 mM $CaCl_2$, 4 mM $MgSO_4$, Trace-Elements consisted of 0.101 g $l^{-1}$ nitrilotriacetic acid pH 6.5, 0.056 g $l^{-1}$ ammonium ferric citrate, 0.01 g $l^{-1}$ $MnCl_2 \times 4$ $H_2O$, 0.002 g $l^{-1}$ $CoCl_2 \times 6$ $H_2O$, 0.001 g $l^{-1}$ $CuCl_2 \times 2$ $H_2O$, 0.002 g $l^{-1}$ boric acid, 0.009 g $l^{-1}$ $ZnSO_4 \times 7$ $H_2O$, 0.001 g $l^{-1}$ $Na_2MoO_4 \times 2$ $H_2O$, 0.002 g $l^{-1}$ $Na_2SeO_3$, 0.002 g $l^{-1}$ $NiSO_4 \times 6$ $H_2O$ with 10 mM lactose as substrate and 2% glycerol as carbon source was used.

As illustrated, to fermenter 1 a constant feed of medium (7 g $l^{-1}$ $NH_4H_3PO_4$, 7 g $l^{-1}$ $K_2HPO_4$, 2 g $l^{-1}$ KOH, 0.37 g $l^{-1}$ citric acid, 1 ml $l^{-1}$ antifoam, 1 mM $CaCl_2$, 4 mM $MgSO_4$, Trace-Elements consist of 0.101 g $l^{-1}$ nitrilotriacetic acid pH 6.5, 0.056 g $l^{-1}$ ammonium ferric citrate, 0.01 g $l^{-1}$ $MnCl_2 \times 4$ $H_2O$, 0.002 g $l^{-1}$ $CoCl_2 \times 6$ $H_2O$, 0.001 g $l^{-1}$ $CuCl_2 \times 2$ $H_2O$, 0.002 g $l^{-1}$ boric acid, 0.009 g $l^{-1}$ $ZnSO_4 \times 7$ $H_2O$, 0.001 g $l^{-1}$ $Na_2MoO_4 \times 2$ $H_2O$, 0.002 g $l^{-1}$ $Na_2SeO_3$, 0.002 g $l^{-1}$ $NiSO_4 \times 6$ $H_2O$) containing 40 mM lactose and 5% glycerol was supplied. Using a New Brunswick parallel fermentation system (BioFlow/CelliGen 115) with a working volume of 1 l, a continuous flow of 20 ml/h feed solution was applied. The action of three synchronous working pumps led then to the similar production of a product stream of 20 ml/h containing almost exclusively 2'-fucosyllactose as sole saccharide product.

Figure 6:
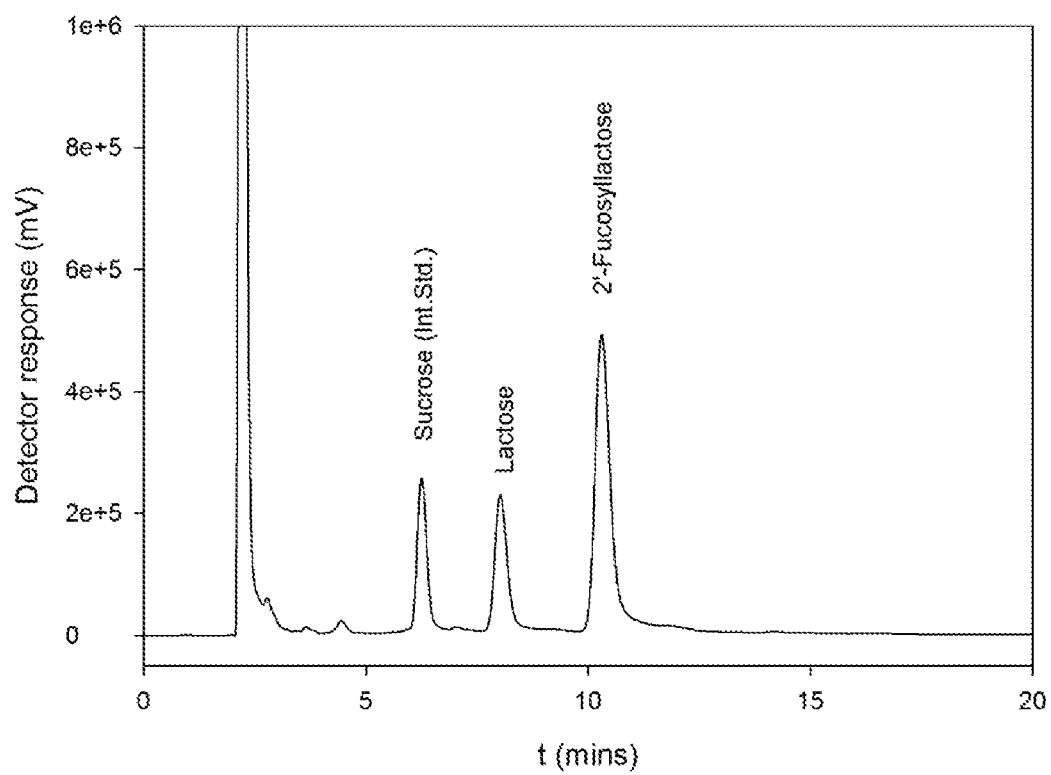
FIG. 6 shows a HPLC analysis of the product stream taken form fermenter 1. The analysis of the cell free fermentation broth shows the presence of both lactose and 2'-fucosyllactose.
Figure 7:
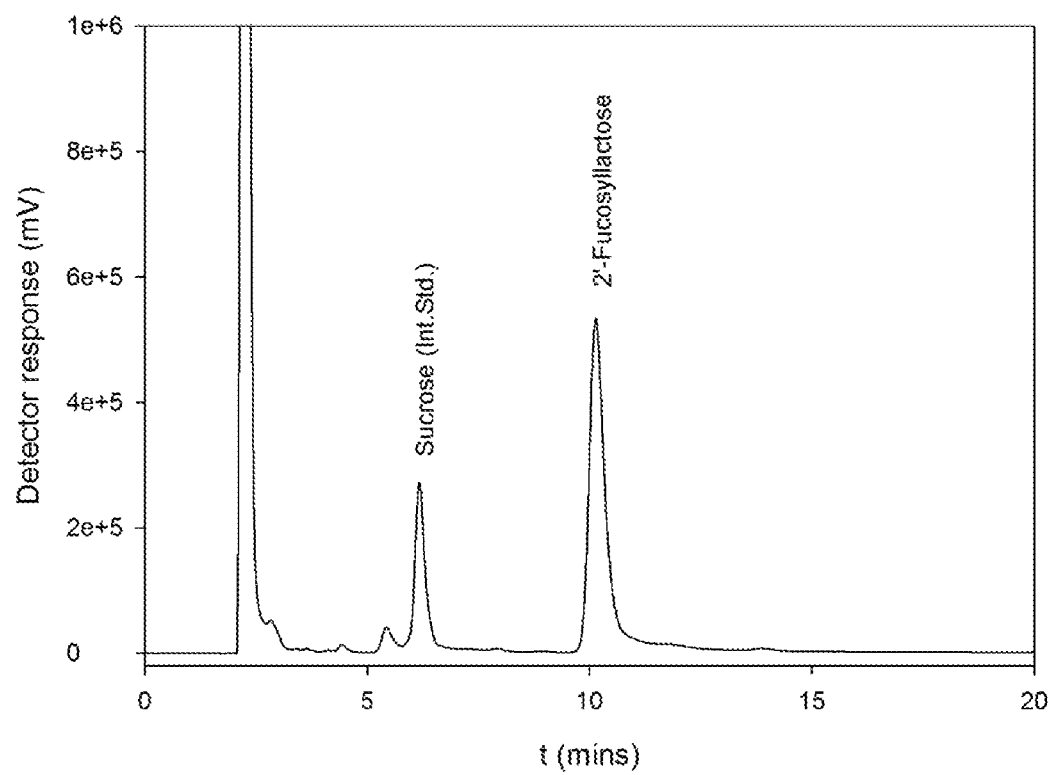
FIG. 7 shows a HPLC analysis of the product stream obtained from fermenter 2. The HPLC analysis shows the lack of the substrate lactose which as metabolized by the strain through the expression of the E. coli lacZ gene encoding a beta-galactosidase and the gal operon for the metabolism of the liberated galactose.

FIG. 6 shows a HPLC analysis of the product stream taken form fermenter 1. The analysis of the cell free fermentation broth shows the presence of both lactose and 2'-fucosyllactose. In contrast, FIG. 7 shows a HPLC analysis of the product stream obtained from fermenter 2. The HPLC analysis shows the lack of the substrate lactose which as metabolized by the strain through the expression of the *E. coli* lacZ gene encoding a beta-galactosidase and the gal operon for the metabolism of the liberated galactose.

Resolution of Saccharide Mixtures by Glycosidase Treatment in the Production of lacto-N-tetraose In the fermentation of lacto-N-tetraose from lactose besides the added substrate also lacto-N-triose II (LNT-2) can accumulate. In order to obtain a more economical fermentation filtrate for purification of lacto-N-tetraose, the specific degradation of lactose and LNT-2 proved desirable.

For this purpose a strain was constructed which, besides the beta-galactosidase, expressed a beta-N-acetylhexosaminidase (encoded by the *Bifidobacterium bididum* JCM1254 bbhI gene) for the specific degradation of LNT-2 into N-acetylglucosamine and lactose. The resulting lactose was further cleaved into glucose and galactose. Whereas the resulting glucose was efficiently metabolized by the organisms the employed *E. coli* BL21 (DE3) strain was incapable of catabolizing galactose due to the DE3 prophage integration into the gal operon. For the efficient degradation of galactose the gal operon from the *E. coli* K strain JM 109 was amplified and transformed into *E. coli* BL21 (DE3) by simultaneous expression of the Lamba Red recombination protein (from an episomal vector system). *E. coli* BL21 transformants capable of galactose degradation were isolated by screening them on galactose containing minimal medium agar plates and McConkey agar plates containing galactose.

After completion of the lacto-N-tetraose fermentation—it is noted that alternatively the oligosaccharide mixture could have been obtained via an enzymatic or chemical synthesis reaction—the engineered glycosidase strain was added to the batch fermentation. Similar to the above described 2'-Fucosyllactose fermentation the degradation of the undesired oligosaccharides were completed within a few minutes to several hours depending on the amounts of culture used for the resolution step.

Figure 8:
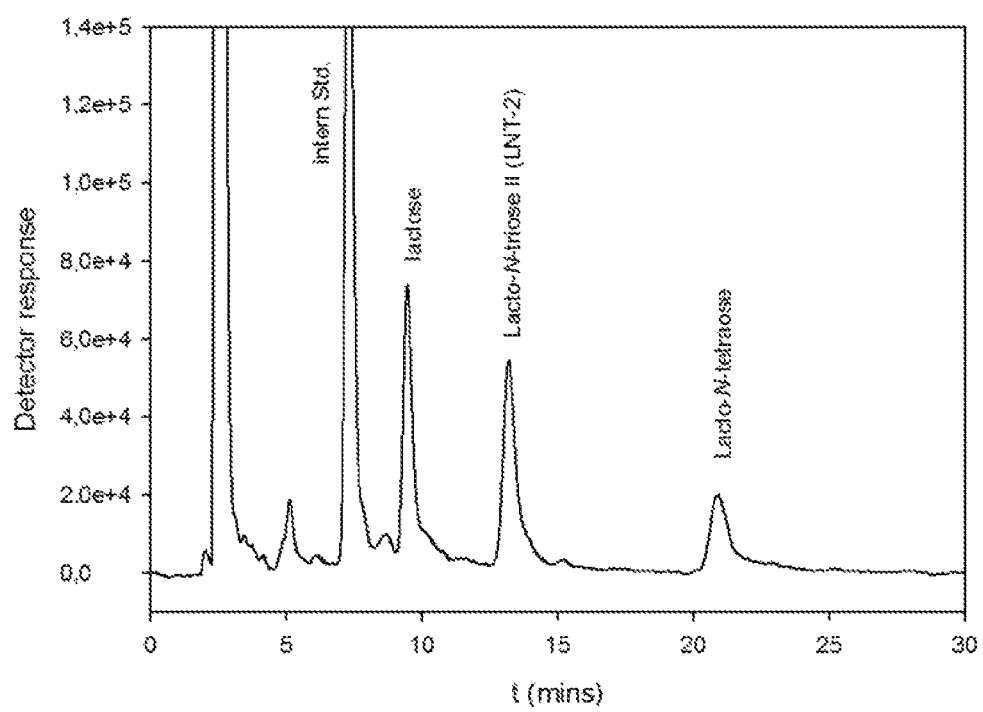
FIG. 8 shows a HPLC analysis of a cell free medium sample prior to the addition of a beta-galactosidase and beta-N-acetyl-hexosaminidase expressing E. coli strain to the fermentation. The strain also expressed the galactose catabolic pathway in order to prevent galactose accumulation.
Figure 9:
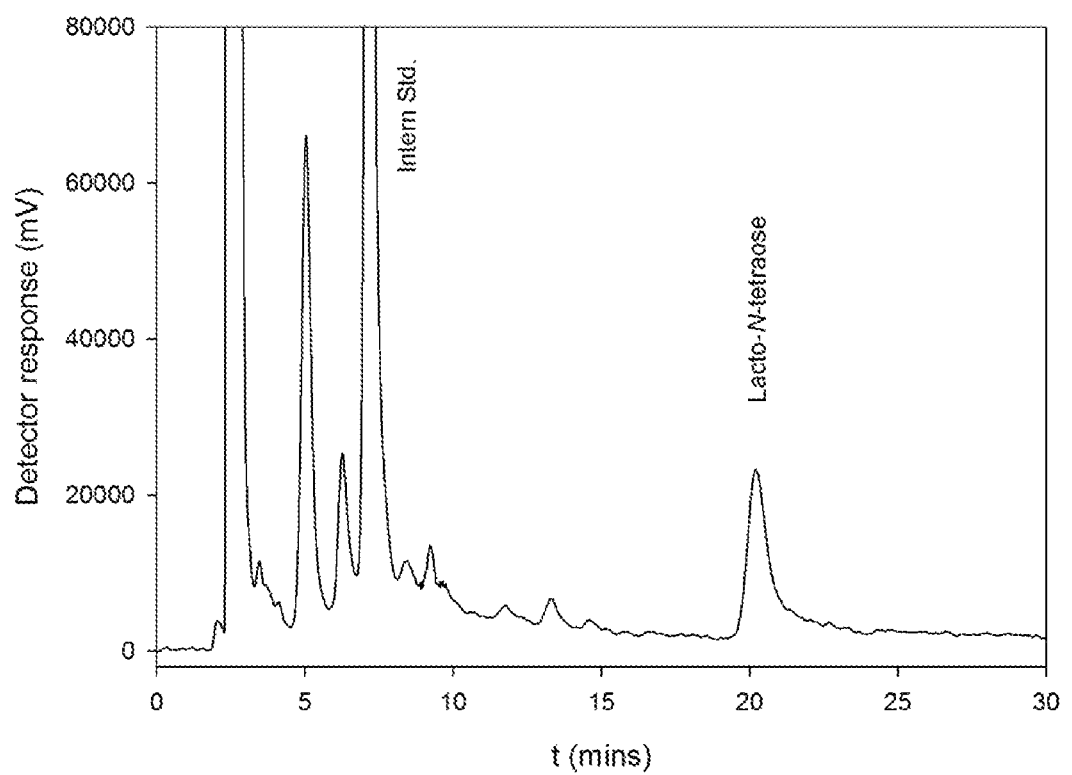
FIG. 9 shows a sample taken after glycosidase and beta-N-acetylhexosaminidase treatment: The comparison of the HPLC chromatograms clearly shows the disappearance of the lactose and Lacto-N-triose II present in the sample before beta-galactosidase and beta-N-acetylhexosaminidase treatment.

The inclusion of the glycosidase resolution step at the end of the fermentative process led to a significant reduction in the complexity of the resulting fermentation filtrate. FIG. 8 shows the analysis of cell free fermentation medium taken before glycosidase and beta-N-acetylhexosaminidase treatment and FIG. 9 shows a sample taken after glycosidase and beta-N-acetylhexosaminidase treatment: The comparison of the HPLC chromatograms clearly shows the disappearance of the lactose and Lacto-N-triose II present in the sample before beta-galactosidase and beta-N-acetylhexosaminidase treatment.

As shown above, the use and the process according to the invention proved particular useful for the purification of human milk oligosaccharides (HMOs) from microbial fermentation reaction. Almost all human milk oligosaccharides contain a Gal-beta-1,4-Glc disaccharide subunit at the reducing end. The lactose moiety (Gal-beta-1,4-Glc) subunit can either be obtained by total fermentation or lactose is added as a substrate to the microbial fermentation. It is often advantageous for attaining maximum volumetric yields to add excess amounts of lactose to the fermentation.

According to the invention, and in order to remove lactose or unwanted side products thereof, a glycosidase such as a beta-galactosidase is added to the fermentation at a specific time point to the fermentation leading to the specific degradation of the lactose and side products.

As mentioned above, alternatively, a transcription-regulated (or otherwise activity regulated) glycosidase can be induced in the production strain or an additional strain expressing the desired activity can be added to the fermentation at a specific time point.

As also mentioned and shown above, the process of the present invention further involves deregulation of sugar catabolic pathways in order to efficiently and effectively remove from the fermentation medium the monosaccharides liberated by the action of the glycosidases. Alternatively, also monosaccharides added as precursors can be equally removed from the fermentation medium by this means.

What is claimed is:

1. A process for producing a 2'-fucosyllactose in a host microorganism, wherein said 2'-fucosyllactose is not naturally occurring in said host microorganism, the process comprising the steps of:
   a) cultivating the host microorganism that produces the 2'-fucosyllactose under conditions and in a fermentation medium suitable for the production of 2' fucosyllactose, thereby producing 2' fucosyllactose and undesired biosynthetic saccharide intermediates;
   b) directly adding an exogenous beta-galactosidase enzyme to the fermentation medium at the end of the cultivation of a) to degrade unused saccharide substrates and/or undesired biosynthetic saccharide intermediates and/or saccharide side products generated during production of the 2' fucosyllactose in step a), and
   c) recovering the 2'-fucosyllactose.

2. The process of claim 1, further comprising centrifuging the cultivated host microorganism to obtain a supernatant and a host microorganism pellet, and recovering the 2'-fucosyllactose from the supernatant.

3. The process of claim 1, wherein the host microorganism is a bacterium or a yeast.

4. The process of claim 3, wherein the host microorganism is an *Escherichia coli* strain, *Lactobacillus* species, a *Corynebacterium glutamicum* strain or a *Saccharomyces* sp. strain.

5. The process of claim 1, wherein the host microorganism overexpresses a salvage pathway for a monosaccharide generated during production of the 2'-fucosyllactose, to convert the monosaccharide into its nucleotide-activated form.

6. The process of claim 1, wherein the host microorganism is a wild-type microorganism modified to overexpress proteins for a galactose catabolic pathway under the control of an inducible promoter.

7. A method for purifying 2'-fucosyllactose from a mixture containing the 2'-fucosyllactose and
   (a) non-desired oligosaccharides or metabolic saccharide products generated during production of said 2'-fucosyllactose, and/or
   (b) unused saccharide substrates used in the production of said 2'-fucosyllactose,
   the method comprising] adding beta-galactosidase to the mixture to degrade the non-desired oligosaccharides or metabolic saccharide products or unused substrates; and recovering the 2'-fucosyllactose from the mixture.

8. The method of claim 7, wherein the 2'-fucosyllactose is produced by in vitro oligosaccharide synthesis or by chemical synthesis or by combinations thereof.

9. The method of claim 7, wherein the 2'-fucosyllactose is a non-naturally occurring oligosaccharide in a host microorganism expressing a beta-galactosidase, and wherein the 2'-fucosyllactose is produced by a microbial fermentation process in the host microorganism.

10. A process for producing 2'-fucosyllactose in a host microorganism, wherein said 2'-fucosyllactose is not naturally occurring in said host microorganism, the process comprising the steps of:
    a) cultivating a host microorganism that can produce 2'-fucosyllactose under conditions and in a medium suitable for the production of 2'-fucosyllactose, thereby producing 2'-fucosyllactose and-undesired biosynthetic saccharide intermediates;
    b) externally adding a beta-galactosidase to the medium following production of the 2'-fucosyllactose in step a) to degrade unused saccharide substrates and/or undesired biosynthetic saccharide intermediates and/or saccharide side products generated during production of the 2'-fucosyllactose in step a), and
    c) recovering the 2'-fucosyllactose;
    wherein the unused saccharide substrate is lactose.

11. The method of claim 1, wherein the host microorganism does not endogenously produce the beta-galactosidase.

12. The method of claim 10, wherein the host microorganism does not endogenously produce the beta-galactosidase.

\* \* \* \* \*

UNITED STATES PATENT AND TRADEMARK OFFICE
CERTIFICATE OF CORRECTION

PATENT NO. : 11,427,845 B2
APPLICATION NO. : 15/067037
DATED : August 30, 2022
INVENTOR(S) : Stefan Jennewein It is certified that error appears in the above-identified patent and that said Letters Patent is hereby corrected as shown below:

In the Claims

In Claim 1, Column 23, Lines 37-38, delete "2' fucosylactose" and insert --2'-fucosylactose--

In Claim 1, Column 23, Line 38, delete "2' fucosylactose" and insert --2'-fucosylactose--

In Claim 1, Column 23, Line 46, delete "2' fucosylactose" and insert --2'-fucosylactose--

In Claim 7, Column 24, Line 37, delete "comprising]" and insert --comprising--

In Claim 10, Column 24, Line 56, delete "and-undesired" and insert --and undesired--

Signed and Sealed this
First Day of November, 2022

*Katherine Kelly Vidal*
Katherine Kelly Vidal
*Director of the United States Patent and Trademark Office*